(12) United States Patent  (10) Patent No.: US 11,518,759 B1
Liang et al.  (45) Date of Patent: Dec. 6, 2022

(54) PROTACS BASED ON VHL LIGAND TARGETING CORONAVIRUS 3CL PROTEASE AND PREPARATION METHOD AND APPLICATION THEREOF

(71) Applicant: SHAANXI PANLONG PHARMACEUTICAL CO., LTD., Xi'an (CN)

(72) Inventors: Chengyuan Liang, Xi'an (CN); Liang Xin, Xi'an (CN); Lei Tian, Xi'an (CN); Juan Xia, Xi'an (CN); Nan Qin, Xi'an (CN); Jingyi Li, Xi'an (CN); Taotao Qiang, Xi'an (CN); Han Li, Xi'an (CN); Xuechuan Wang, Xi'an (CN); Xiaolin Xie, Xi'an (CN); Dezhu Zhang, Xi'an (CN); Qingbo Zhao, Xi'an (CN); Zhenfeng Shi, Xi'an (CN); Min Li, Xi'an (CN); Shaojun Zhang, Xi'an (CN); Kangxiong Wu, Xi'an (CN); Catherine J Lee, Atlanta, GA (US); Maggie Lewis, North Decatur, GA (US); Zhao Ma, Xi'an (CN); Xuhua Zhou, Xi'an (CN)

(73) Assignee: SHAANXI PANLONG PHARMACEUTICAL CO., LTD., Shaanxi (CN)

( * ) Notice: Subject to any disclaimer, the term of this patent is extended or adjusted under 35 U.S.C. 154(b) by 0 days.

(21) Appl. No.: 17/847,393

(22) Filed: Jun. 23, 2022

(30) Foreign Application Priority Data

Apr. 19, 2022 (CN) .......................... 202210412066.6

(51) Int. Cl.
  *C07D 417/14* (2006.01)
(52) U.S. Cl.
  CPC .................... *C07D 417/14* (2013.01)
(58) Field of Classification Search
  CPC ..................................... C07D 417/14
  USPC ......................................... 514/245
  See application file for complete search history.

(56) References Cited

U.S. PATENT DOCUMENTS 11,207,370 B2 * 12/2021 Schinazi .............. A61K 31/519

* cited by examiner

Primary Examiner — Kahsay Habte

(57) ABSTRACT

A compound of formula I or formula II, a pharmaceutically acceptable salt, or a tautomer thereof is disclosed.

formula I

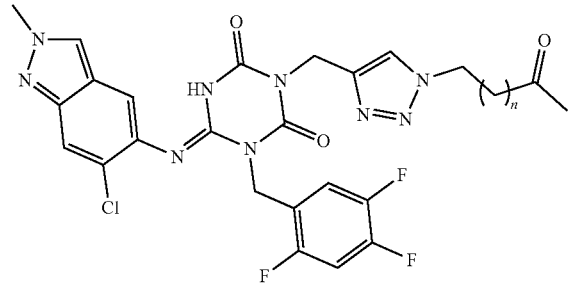

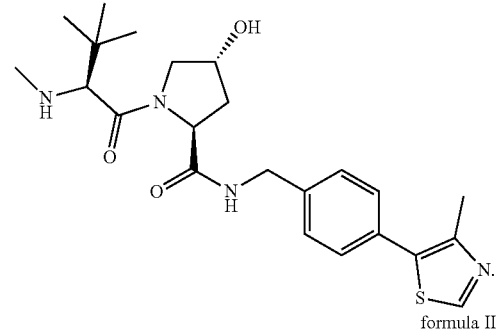

formula II

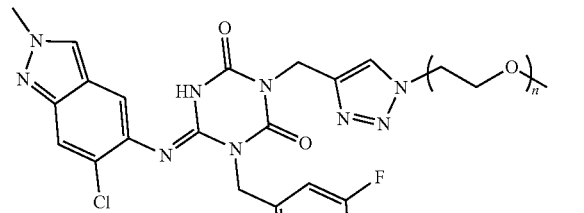

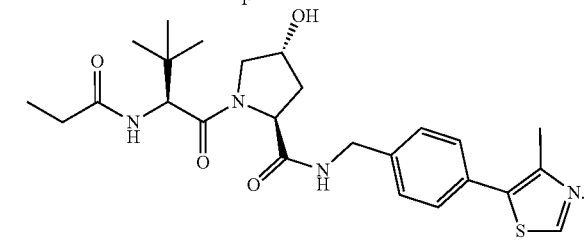

In formula I and II, n is 1-6.

4 Claims, No Drawings

PROTACS BASED ON VHL LIGAND TARGETING CORONAVIRUS 3CL PROTEASE AND PREPARATION METHOD AND APPLICATION THEREOF

The present application claims priority to Chinese Patent Application No. 202210412066.6, filed on Apr. 19, 2022, which is incorporated by reference for all purposes as if fully set forth herein.

TECHNICAL FIELD

The invention belongs to the technical field of medicinal chemistry, and in particular relates to a PROTACs based on VHL ligand targeting coronavirus 3CL protease and a preparation method and application thereof.

BACKGROUND TECHNIQUE

COVID-19 (new coronavirus pneumonia) is highly contagious and highly pathogenic, and its mutant strains Delta and Omicron have stronger transmission ability. The endless mutant strains make the global epidemic situation more complicated. The novel coronavirus has posed a serious threat to human health, social stability and economic development.

$3CL^{pro}$ (3C-like protease, also known as major protease $MP^{pro}$), as an important non-structural protein in coronaviruses, has a cleavage site similar to the 3C protease of microRNA virus, and plays an important role in the replication and transcription of progeny viruses. $3CL^{pro}$ has three domains. Domains I and II are mainly composed of β-sheet structure, and domain III is mainly composed of α-helix structure. The active site is located in the groove formed between domains I and II. Domain III is involved in dimer formation. Compared with domain III, the sequence conservation of domain I and domain II of different coronaviruses is higher, which is consistent with their active sites being located in the first two domains. $3CL^{pro}$ uses conservative cysteine and histidine as catalytic amino acids to form a catalytic duplex, in which cysteine is a nucleophilic attack group and histidine is a basic group. Coronavirus $3CL^{pro}$ is essential for viral replication and highly conserved, making it an ideal anti-coronavirus drug target.

Proteolytic targeting chimeric molecules (PROTACs) are one of the most disruptive technologies in drug development in recent years. Proteolytic targeted chimera (PROTAC) is a technique for chemically degrading proteins. It can bind the target protein and E3 ubiquitin ligase at the same time, make the target protein close to E3 ubiquitin ligase, ubiquitinate the target protein, and then degrade the target protein through the degradation of the ubiquitinproteasome system (UPS). It is worth mentioning that, regardless of the function of the target protein, it can be degraded by PROTAC technology.

SUMMARY OF THE INVENTION

In one embodiment, the present application discloses a compound of formula I or formula II, a pharmaceutically acceptable salt, a diastereomer, or a tautomer thereof:

formula I 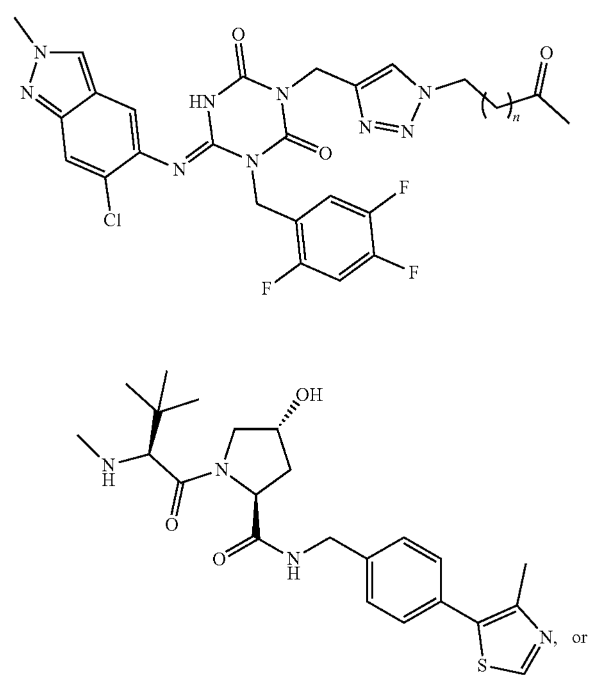 or formula II

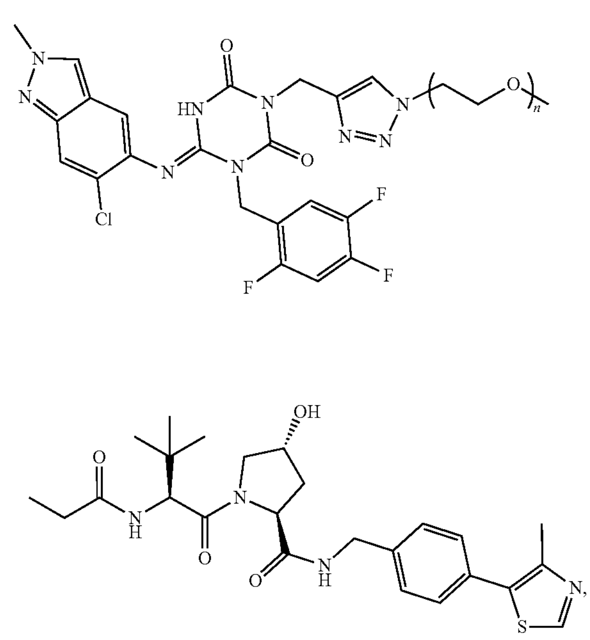

In formulas I and II, n is 1-6.

In another embodiment, the compound is selected from the group consisting of:
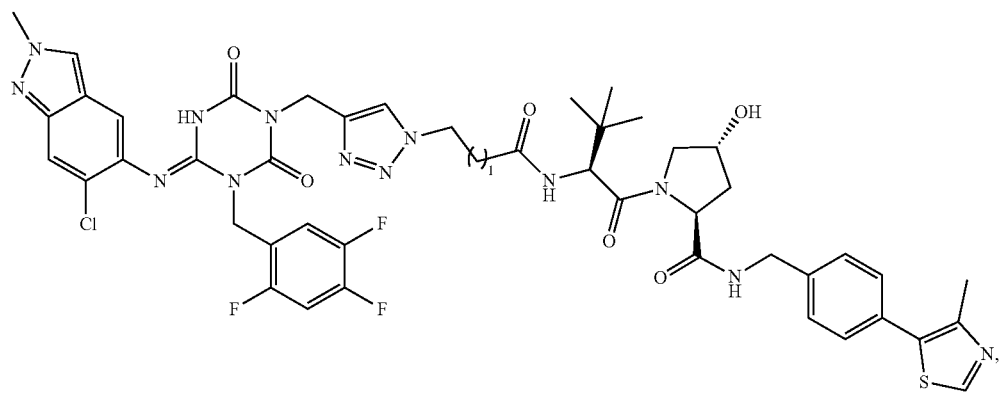
1
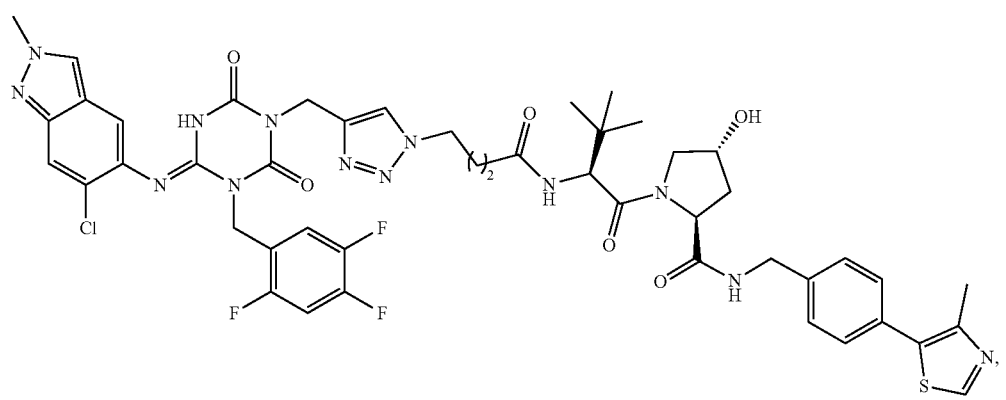
2
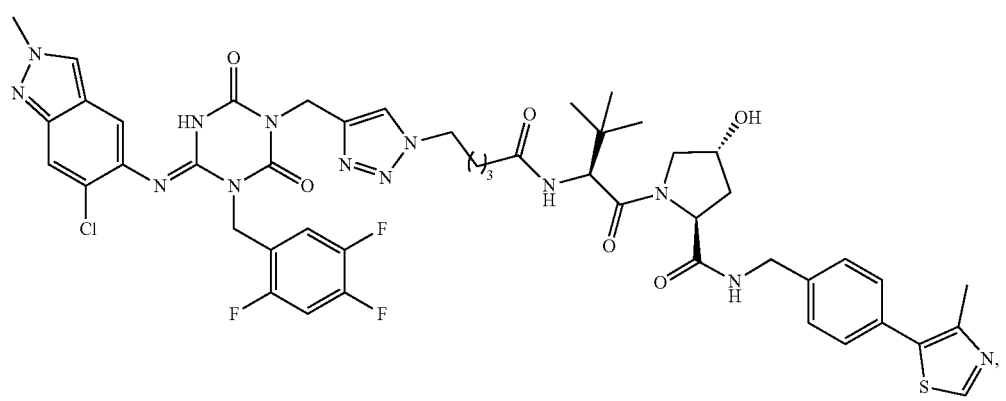
3
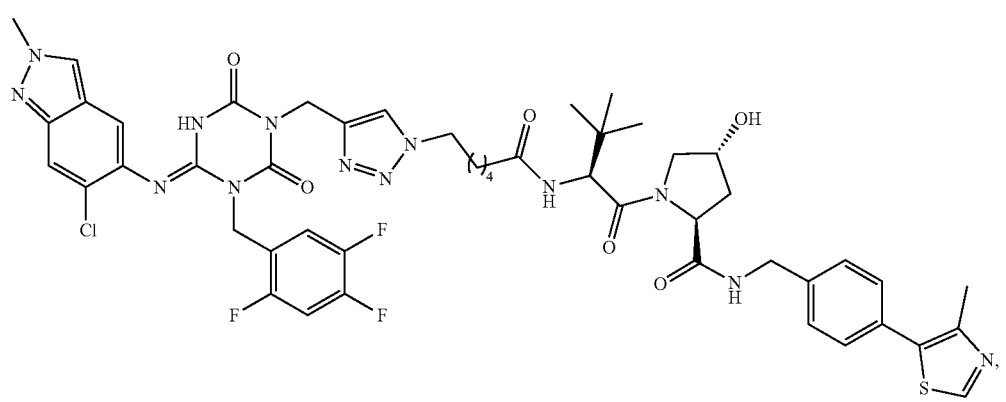
4

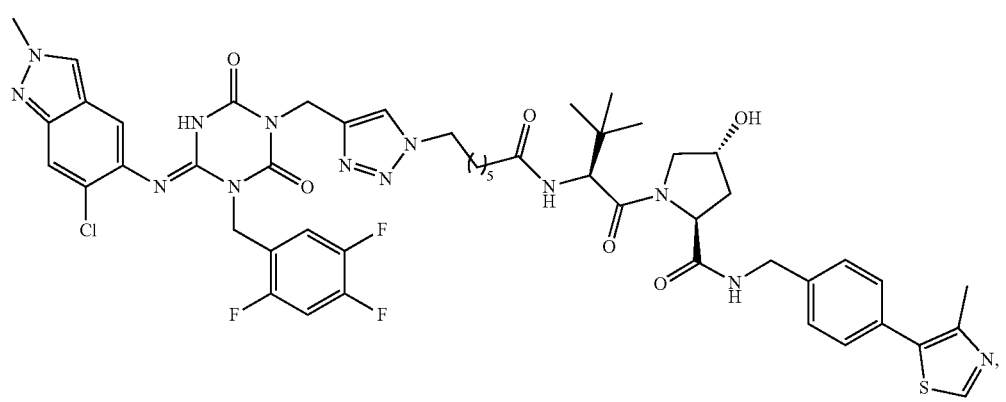
5
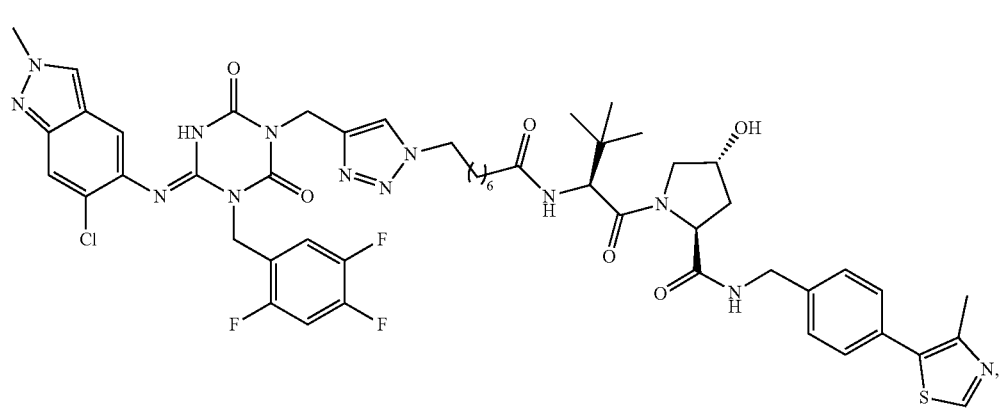
6
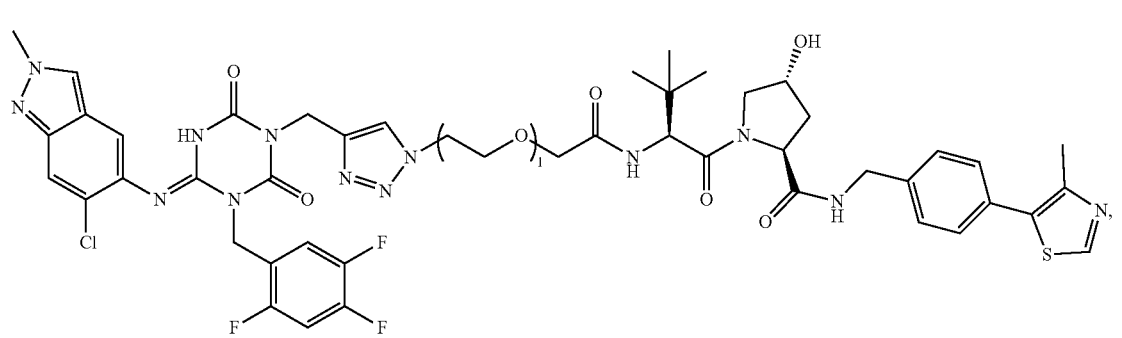
7
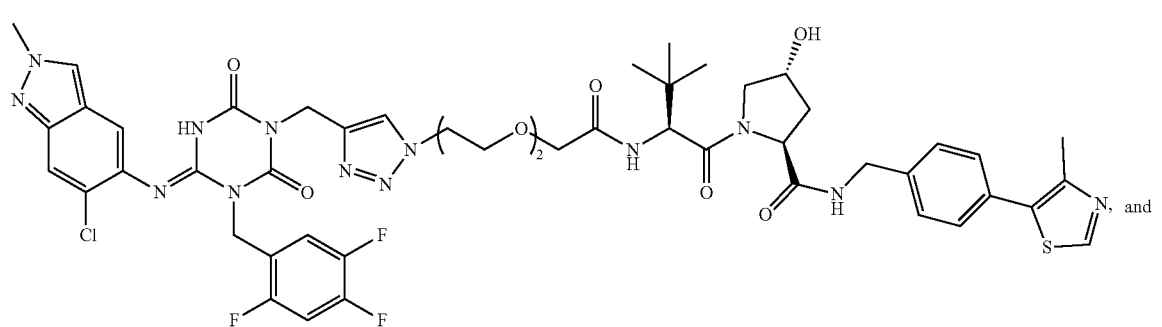
8

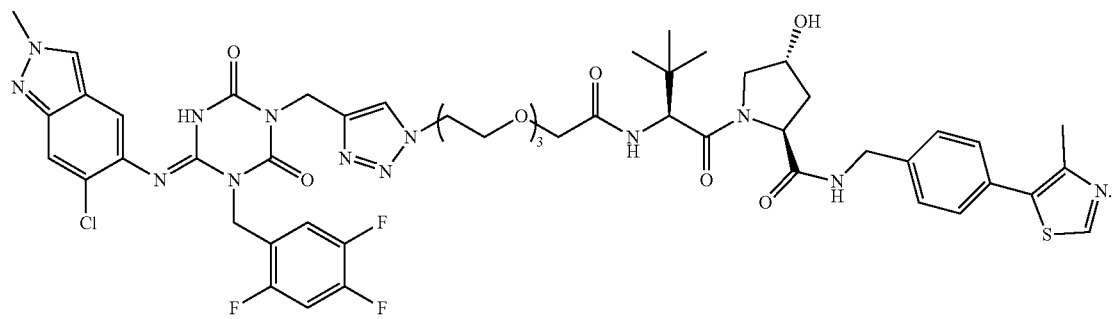

In another embodiment, the pharmaceutically acceptable salt includes one selected from the group consisting of hydrochloric acid, hydrobromic acid, sulfuric acid, nitric acid, phosphoric acid, acetic acid, fumaric acid, maleic acid, oxalic acid, malonic acid, succinic acid, citric acid, malic acid, methanesulfonic acid, ethanesulfonic acid, benzenesulfonic acid, toluenesulfonic acid, glutamic acid, and aspartic acid.

In another embodiment, the present application discloses an anti-coronavirus pharmaceutical preparation that includes the compound of present application.

In another embodiment, the coronavirus is novel coronavirus SARS-CoV-2.

Compared with the prior art, the present invention has the following beneficial effects:

The present invention provides PROTACs based on VHL ligand targeting coronavirus 3CL protease, selects VHL ligand (S, R, S)-AHPC as E3 ligase ligand, and uses different types and different chain length linkers to connect the coronavirus 3CL protease inhibitor with E3 ligase. PROTACs targeting the coronavirus 3CL protease were successfully prepared, which could effectively target the target protein. The 3CL$^{pro}$ inhibitory activity test results show that the compounds synthesized in the present invention have a strong inhibitory effect on 3CL$^{pro}$, and the IC$_{50}$ values of compounds 4, 5, 6, 8 and 9 on 3CL$^{pro}$ are all below 100 nM; the 3CL$^{pro}$ degradation activity test results show that the compounds all have degrading activity to 3CL$^{pro}$. The DC$_{50}$ values of compounds 5, 6 and 8 for 3CL$^{pro}$ are all below 100 nM. The compounds overcome the defects of the existing coronavirus 3CL protease inhibitors, such as single structure type, limited pharmacodynamic pathway.

The invention provides a preparation method of PROTACs containing VHL ligand targeting coronavirus 3CL protease. To obtain the target product, all reactions avoid the use of high temperature, high pressure and highly toxic reagents, and can be carried out under relatively mild conditions, with low requirements for reaction equipment and low environmental pollution; at the same time, the atom economy is high, suitable for industrial production.

DETAILED DESCRIPTION

In order to make those skilled in the art better understand the solutions of the present invention, the technical solutions in the embodiments of the present invention will be clearly and completely described below with reference to the accompanying drawings in the embodiments of the present invention. Obviously, the described embodiments are only Embodiments are part of the present invention, but not all of the embodiments. Based on the embodiments of the present invention, all other embodiments obtained by persons of ordinary skill in the art without creative efforts shall fall within the protection scope of the present invention.

It should be noted that the terms "first," "second" and the like in the description and claims of the present invention and the above drawings are used to distinguish similar objects, and are not necessarily used to describe a specific sequence or sequence. It is to be understood that the data so used may be interchanged under appropriate circumstances such that the embodiments of the invention described herein can be practiced in sequences other than those illustrated or described herein. Furthermore, the terms "comprising" and "having," and any variations thereof, are intended to cover non-exclusive inclusion, for example, a process, method, system, product or device comprising a series of steps or units is not necessarily limited to those expressly listed Rather, those steps or units may include other steps or units not expressly listed or inherent to these processes, methods, products or devices.

Below in conjunction with accompanying drawing, the present invention is described in further detail:

PROTACs containing VHL ligand targeting coronavirus 3CL protease provided by the present invention are compounds represented by formula I or formula II, pharmaceutically acceptable salts thereof, diastereomers thereof, or tautomers thereof.

The structural formula of the compound of formula I or formula II is:

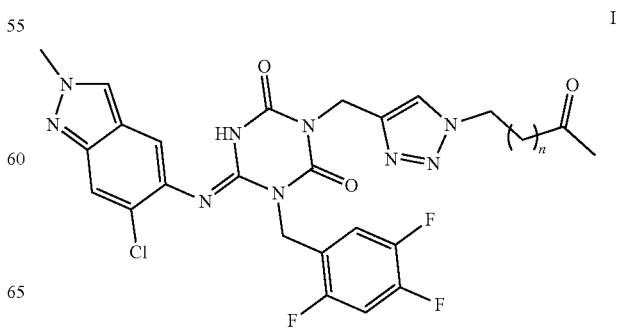

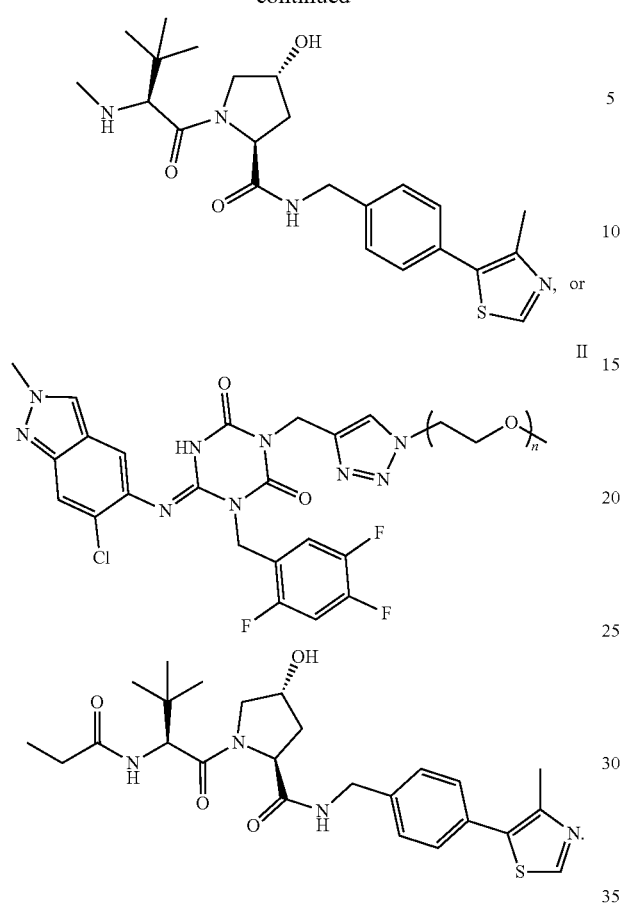

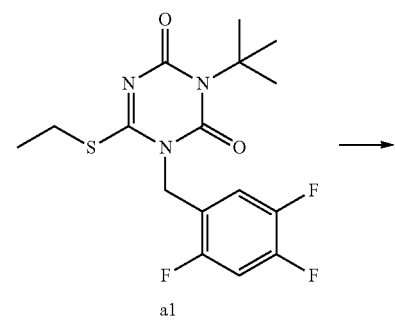

a1

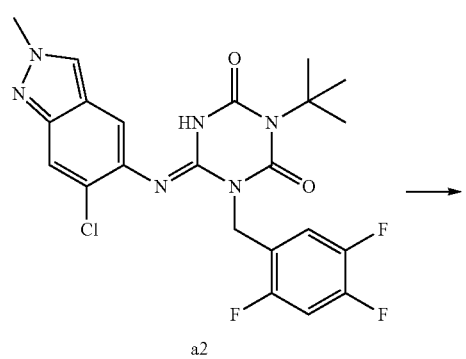

a2

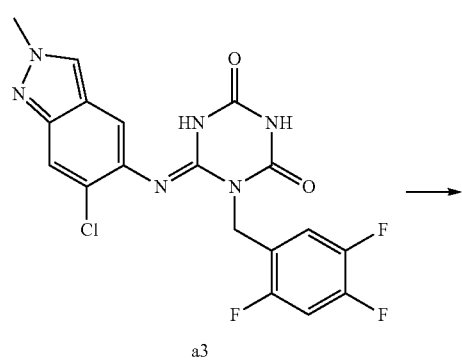

a3

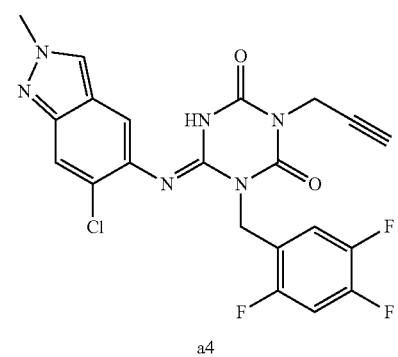

a4

In formulas I and I, n=1-6;

The pharmaceutically acceptable salt can be a salt of hydrochloric acid, hydrobromic acid, sulfuric acid, nitric acid, phosphoric acid, acetic acid, fumaric acid, maleic acid, oxalic acid, malonic acid, succinic acid, lemon. acid, malic acid, methanesulfonic acid, ethanesulfonic acid, benzenesulfonic acid, toluenesulfonic acid, glutamic acid or aspartic acid.

The preparation method of the compounds of the present application is as follows:

(1) 3-Tert-butyl-6-(ethylthio)-1,3,5-triazine-2,4(1H,3H)-dione is used as starting material, and 2,4,5-trifluoro benzyl bromide is alkylated to obtain compound a1; then 6-chloro-2-methyl-2H-indazole unit is introduced into the 6-position of the triazine nucleus to obtain compound a2; the tert-butyl group at the 3-position of the triazine nucleus of compound a2 is removed in an acidic solvent to obtain compound a3; then a 3-propynyl group is introduced into the 3-position of the triazine nucleus of compound a3 to finally obtain compound a4. The reaction scheme is as follows:

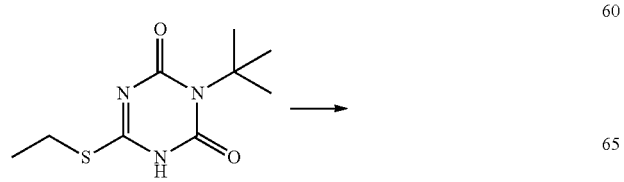

The solvent used in the synthesis process of compound a1 is acetonitrile. A molar ratio of 3-tert-butyl-6-(ethylthio)-1,3,5-triazine-2,4(1H,3H)-dione and 2,4,5-trifluorobenzyl bromide is 1:1.1. The reaction is carried out with potassium carbonate and under heating and refluxing conditions. In the synthesis process of compound a2, a molar ratio of compound a1 and 6-chloro-2-methyl-2H-indazol-5-amine is 1:1.3, the reaction temperature is 0° C., the solvent used is tetrahydrofuran, and the catalyst used is lithium bistrimethylsilyl amide (LiHMDS). The acid solvent used in the synthesis process of compound a3 is trifluoroacetic acid (TFA). In the synthesis of compound a4, a molar ratio of compound a3 and 3-bromopropyne is 1:1.2, the solvent used is N,N-dimethylformamide (DMF), and the reaction temperature is 60° C.

(2) (S,R,S)-AHPC (MDK7526, VH032-NH2, VHL LIGAND 1) (purchased from Shanghai McLean Biochemical Technology Co., Ltd.; CAS No. 1448297-52-6) is used as starting material, and reacts with bromoalkanoic acids of different lengths in an acid-amine condensation reaction to obtain the corresponding compounds b1-b6, and then a reaction with sodium azide under the catalysis of potassium iodide results the corresponding compounds c1-c6.

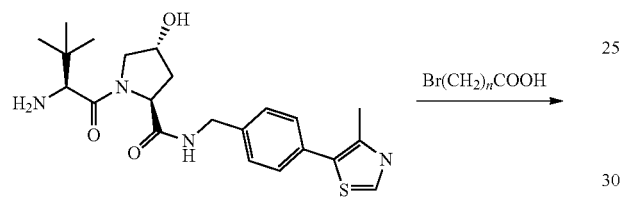

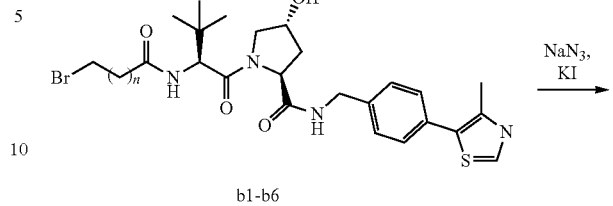

b1-b6

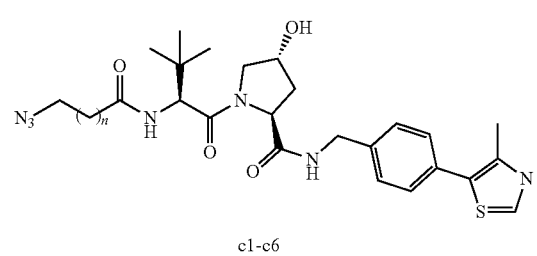

c1-c6

Or, (S,R,S)-AHPC (MDK7526, VH032-NH2, VHL LIGAND 1) is used as starting material to carry out an acid amine condensation reaction with azide-polyethylene glycol-acetic acid compound to obtain corresponding compound d1-d3.

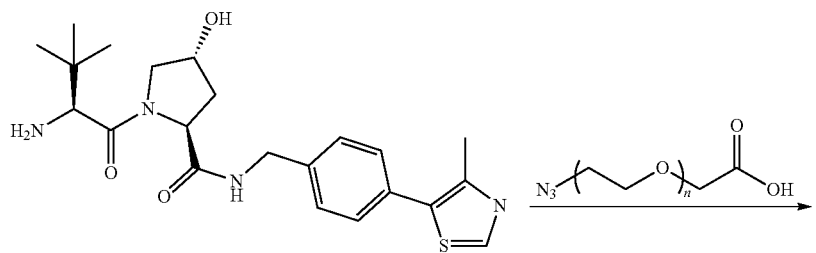

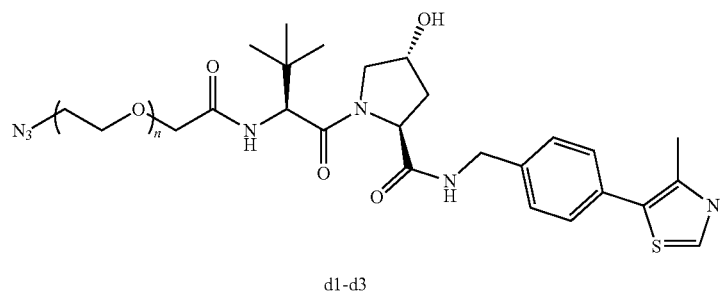

d1-d3

In the synthesis of the compounds b1-b6, a molar ratio of (S,R,S)-AHPC and bromoalkanoic acid is 1:1.2. The bromoalkanoic acid is dissolved in dichloromethane (DCM) and the condensing agent used is 2-(7-azobenzotriazole)-N,N,N',N'-tetramethylurea hexafluorophosphoric acid ester (HATU). The solvent used in the synthesis of compounds c1-c6 is DMF, a molar ratio of compounds b1-b6 and sodium azide is 1:3, and the catalyst used is potassium iodide. In the synthesis of the compounds d1-d3, a molar ratio of (S,R,S)-AHPC and azide-polyethylene glycol-acetic acid compound is 1:2, the condensing agent used is thionyl chloride, and the solvent is tetrahydrofuran.

(3) Compound a4 reacts with compounds c1-c6 to obtain compounds of formula I.

Alternatively, compound a4 reacts with compounds d1-d3 to obtain compounds of formula II.

The reaction scheme is as follows:

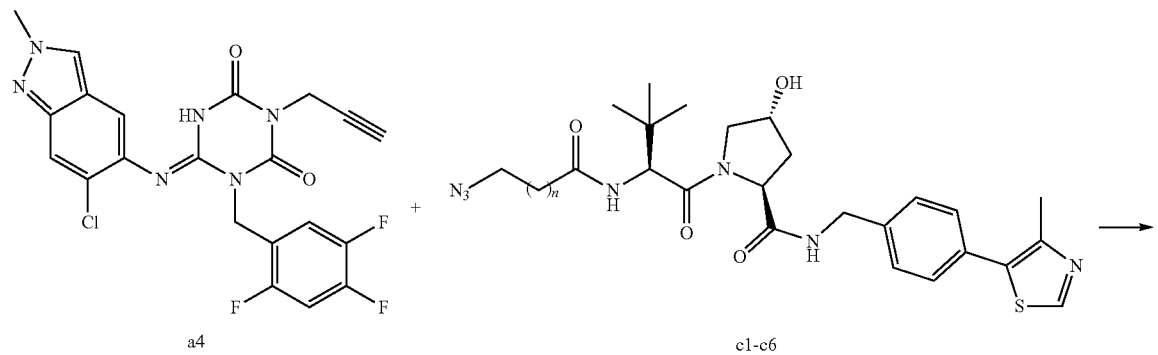

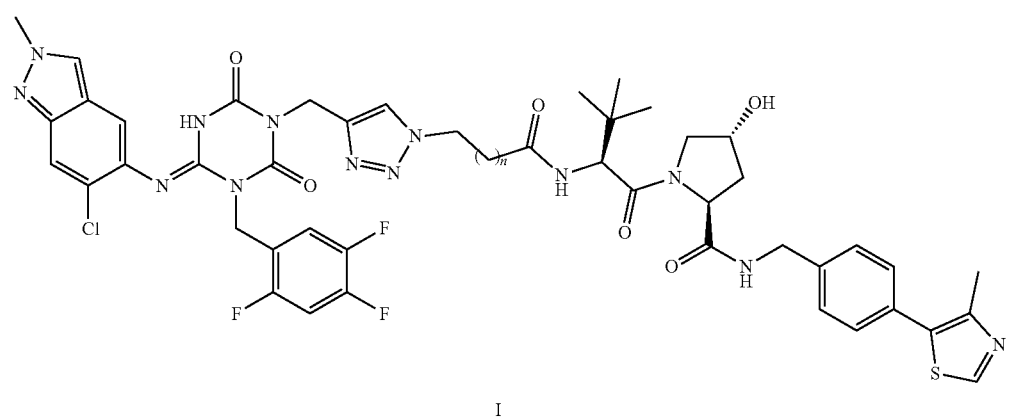

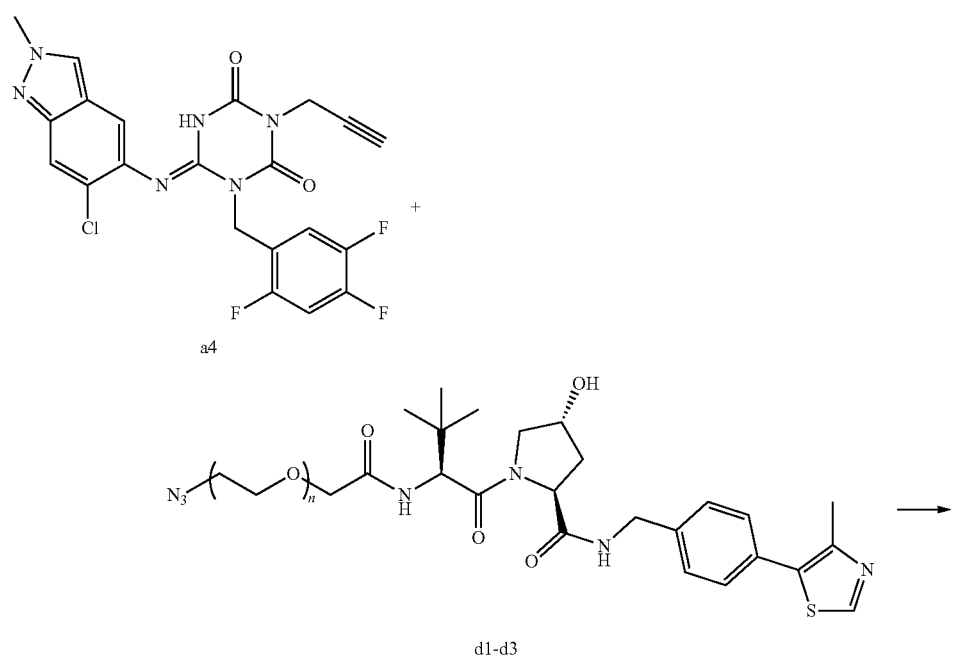

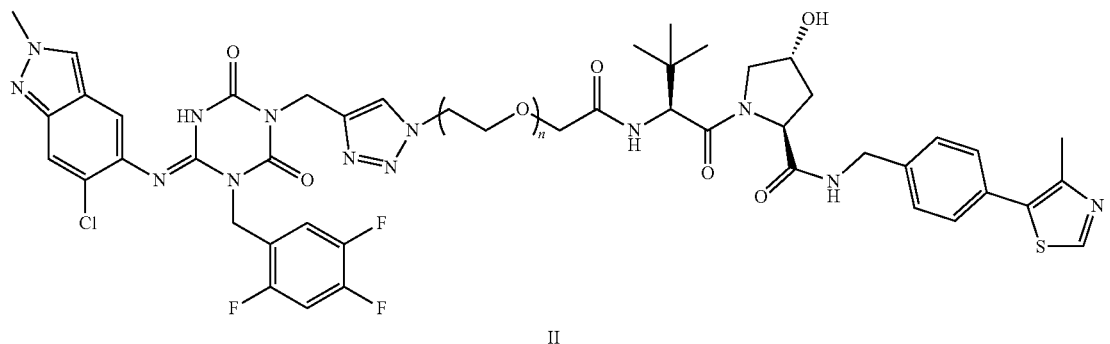

II

A molar ratio of compound a4 to c1-c6 or d1-d3 in the reaction is 1:1.2, the solvent used in the reaction is a mixture of tetrahydrofuran and water, and a volume ratio of tetrahydrofuran:water is 10:1; the catalyst is copper sulfate pentahydrate and sodium ascorbate; reaction is conducted at 45° C. under argon protection.

1. Specific Examples of Synthetic Compounds 1-9

The structural formulas of the representative compounds of the present invention are as follows:

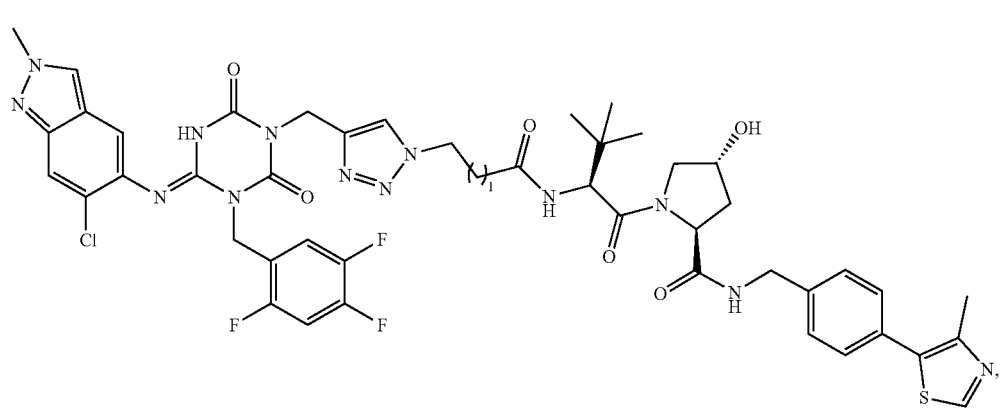

1

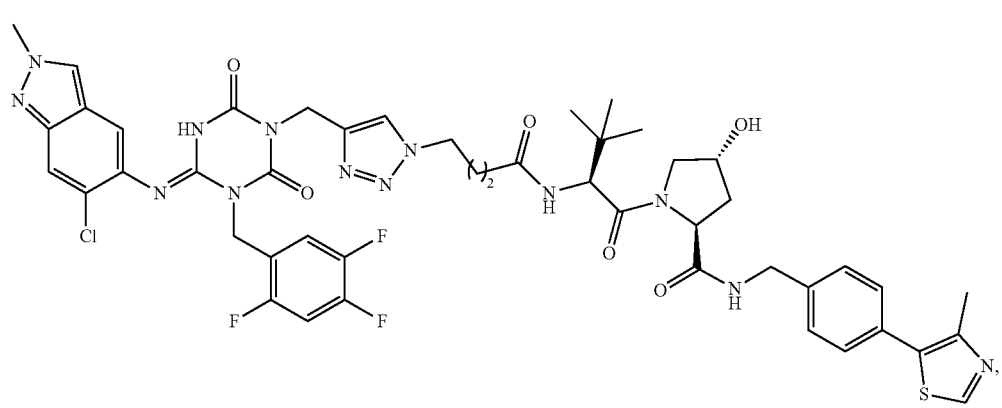

2

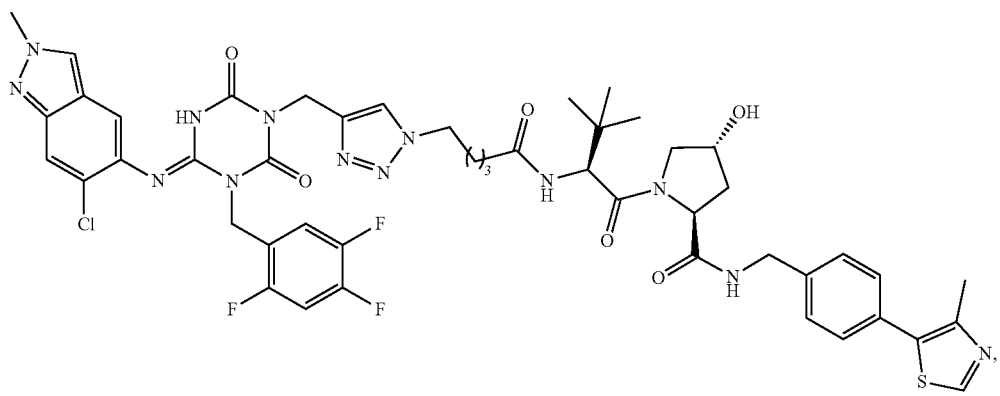
3
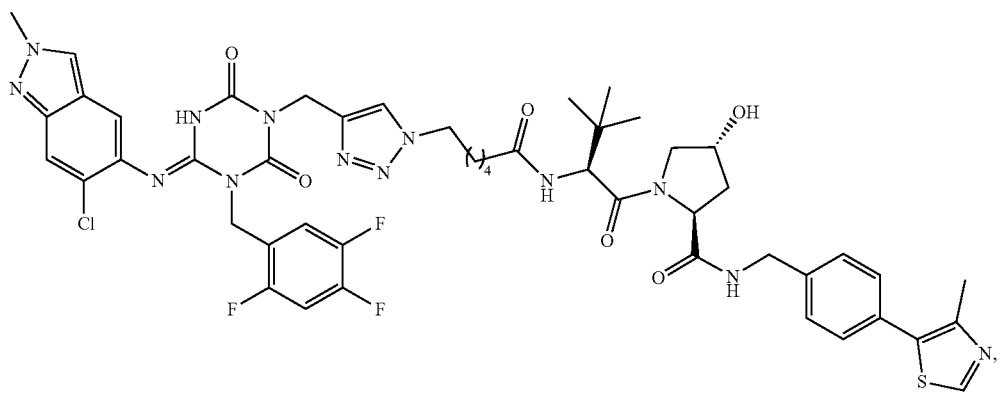
4
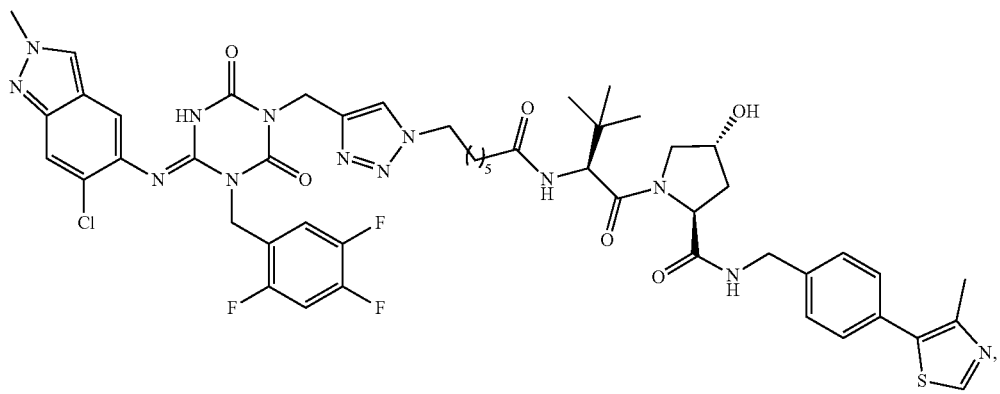
5
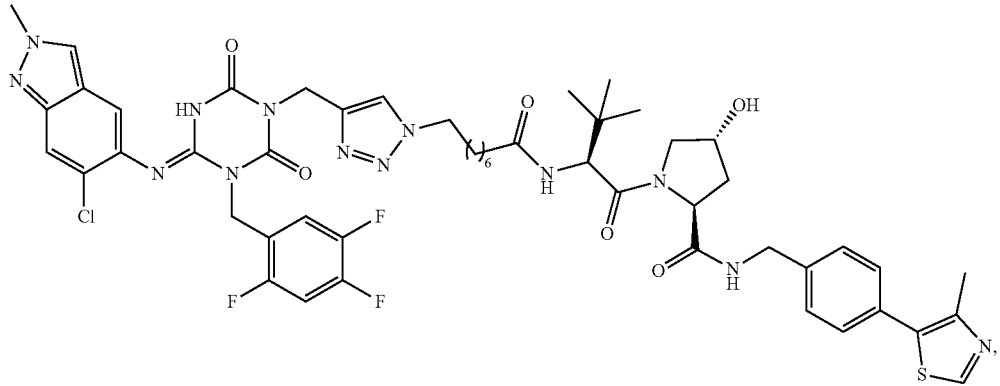
6

-continued
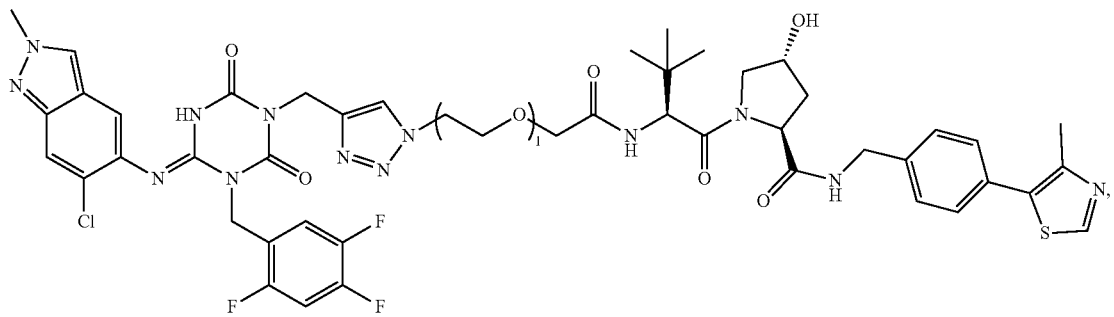
7
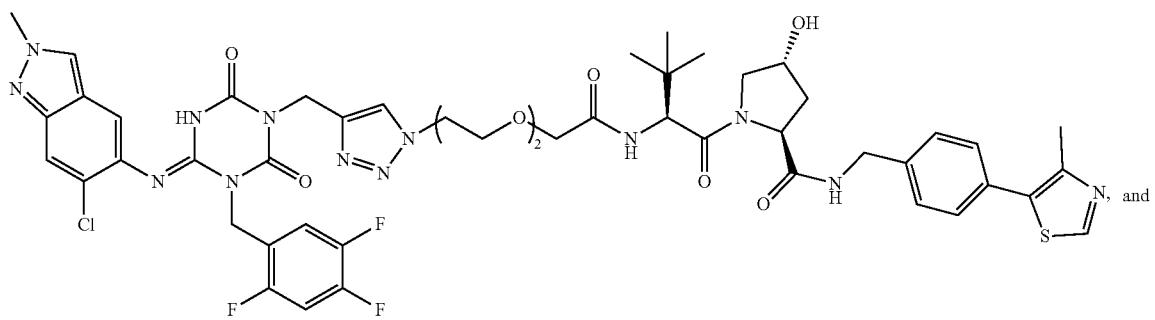
8, and
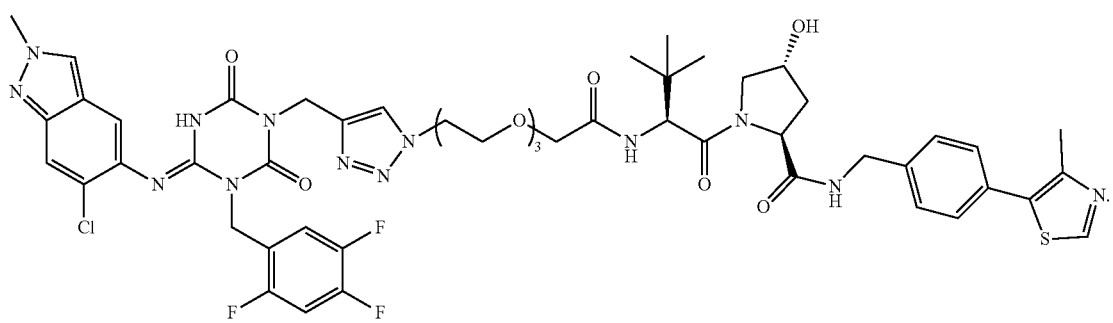
9.
Examples of the synthesis of the above compounds are given below.
Example 1
Compound 1: Preparation of (2 S,4R)-1-((S)-2-(3-(4-(((E)-4-(6-chloro-2-methyl-2H-indazol-5-yl)idene amino)-2,6-dioxy-3-(2,4,5-trifluorobenzyl)-1,3,5-triazin-1-yl)methyl)-1H-1,2,3-triazol-1-yl)propionamido)-3,3-dimethylbutyryl)-4-hydroxy-N-(4-(4-methylthiazol-5-yl)benzyl)pyrrolidine-2-carboxamide
(1) Preparation of Compound a4
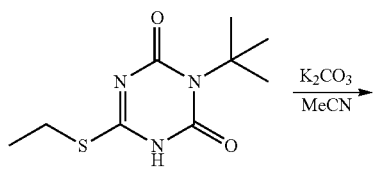
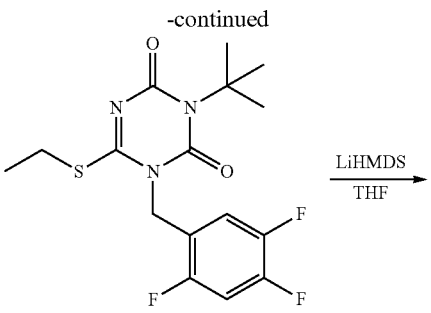
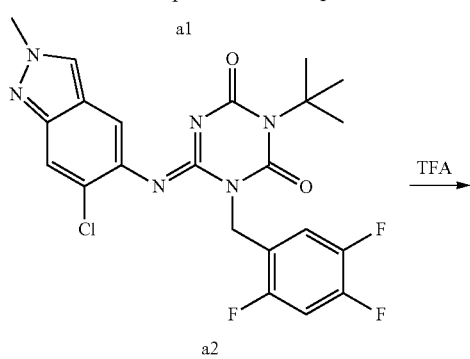

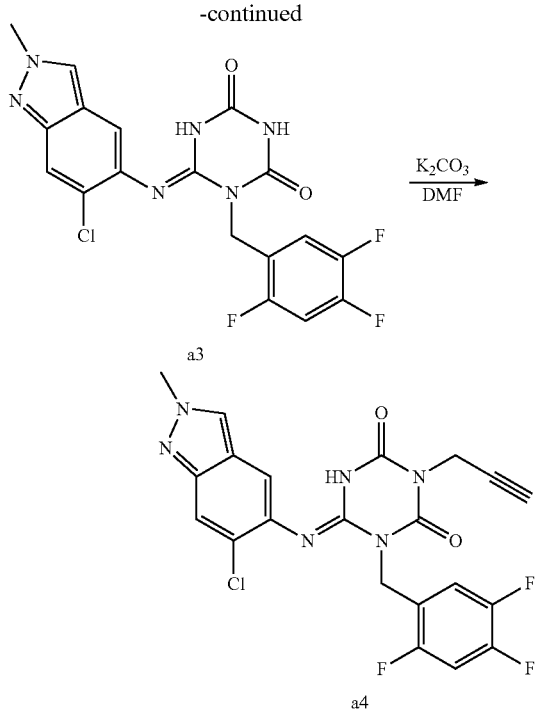

Step 1: Synthesis of Compound a1

3-tert-Butyl-6-(ethylthio)-1,3,5-triazine-2,4(1H,3H)-dione (114.7 mg, 0.5 mmol), 2,4,5-triazine fluorobenzyl bromide (123.8 mg, 0.55 mmol) and potassium carbonate (79.6 mg, 0.48 mmol) were placed in a reactor, dissolved in 10 mL of acetonitrile, heated to reflux, stirred for 3 hours, and monitored by TLC. After the reaction was complete, the reaction mixture was concentrated under reduced pressure to remove the solvent, the obtained solid residue was washed with saturated aqueous sodium chloride solution, extracted with ethyl acetate, the organic phase was collected, and separated and purified by column chromatography (n-hexane:ethyl acetate (V:V)=8:2) as mobile phase), and dried to obtain 161.0 mg of compound a1, a yield of 86.24%.

Step 2: Synthesis of Compound a2

Compound a1 (186.7 mg, 0.5 mmol) and 6-chloro-2-methyl-2H-indazol-5-amine (118.1 mg, 0.65 mmol) were placed in a reactor, and dissolved in 5 mL of tetrahydrofuran. A solution of 1 mmol lithium bistrimethylsilylamide (LiHMDS) (0.2 mL, 1 mmol) in tetrahydrofuran was slowly added to the reactor at 0° C., and the reaction was stirred for 3 hours and monitored by TLC. After the reaction was completed, the reaction mixture was cooled to room temperature, quenched by adding an aqueous ammonium chloride solution, and the reaction solution was concentrated under reduced pressure to remove tetrahydrofuran. The resulting residue was washed with saturated aqueous sodium chloride solution, extracted with ethyl acetate, and the organic phase was collected and separated by column chromatography. Purification (dichloromethane:methanol (V:V)=10:1 as mobile phase) gave 62.2 mg of compound a2, a yield is 25.24%.

Step 3: Synthesis of Compound a3

Compound a2 (246.4 mg, 0.5 mmol) was placed in a reactor, 3 mL of trifluoroacetic acid (TFA) was added, stirred at room temperature overnight, then azeotropically concentrated with toluene under reduced pressure to remove the solvent, and dried to obtain 202.1 mg of compound a3, a yield of 92.52%.

Step 4: Synthesis of Compound a4

Compound a3 (218.4 mg, 0.5 mmol), 3-bromopropyne (43 μL, 0.6 mmol) and potassium carbonate (82.9 mg, 0.6 mmol) were placed in a reactor with 10 mL N,N-dimethylmethane. The reaction mixture was heated and stirred at 60° C. for 5 hours, and monitored by TLC. After the reaction was complete, the reaction mixture was washed with saturated aqueous sodium chloride solution, extracted with ethyl acetate, the organic phase was collected, separated and purified by column chromatography (n-hexane:ethyl acetate (V:V)=6:4 as mobile phase). After drying, 148.2 mg of compound a4 was obtained, a yield of 62.43%.

(2) Preparation of compound c1

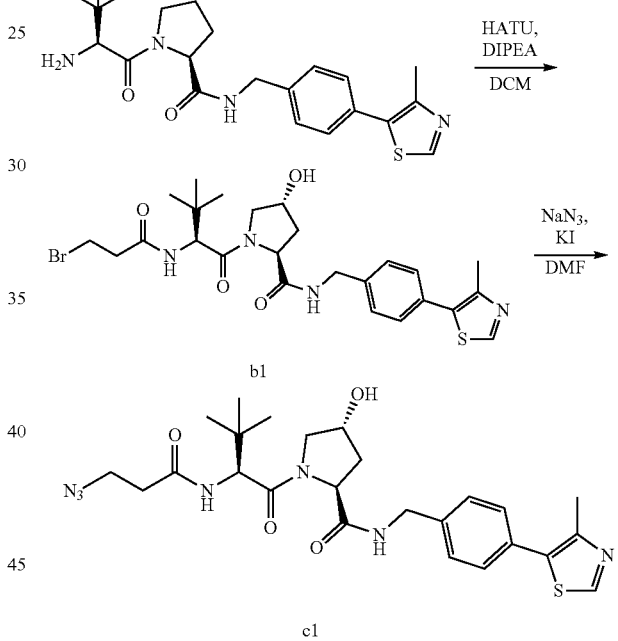

Step 1: Synthesis of Compound b1

3-Bromopropionic acid (91.8 mg, 0.6 mmol) was dissolved in 3 mL of dichloromethane and placed in a reactor. HATU (380.2 mg, 1 mmol) and DIPEA (260 μL, 1.5 mmol) were added. The reaction mixture was stirred for 1 hour. (S,R,S)-AHPC (215.3 mg, 0.5 mmol) was dissolved in 3 mL of dichloromethane, added dropwise to the reactor. The reaction mixture was then stirred at room temperature for 5 hours and monitored by TLC. After the reaction was complete, the reaction mixture was concentrated under reduced pressure to remove dichloromethane, and the obtained solid residue was washed with saturated aqueous sodium chloride solution, extracted with ethyl acetate, the organic phase was collected. 230.6 mg of compound b1 was separated and purified by column chromatography (dichloromethane:methanol (V:V)=10:1 as mobile phase), a yield of 81.55%.

Step 2: Synthesis of Compound c1

Compound b1 (282.8 mg, 0.5 mmol), sodium azide (97.5 mg, 1.5 mmol) and potassium iodide (8.3 mg, 0.05 mmol) were placed in a reactor with 10 mL of N,N-dimethylformamide. The mixture was heated and stirred at 70° C. for 5 hours, and monitored by TLC. After the reaction was complete, the reaction mixture was washed with saturated aqueous sodium chloride solution, extracted with ethyl acetate, and the organic phase was collected and dried to obtain 218.3 mg of compound c1, a yield of 82.74%.

(4) Preparation of compound 1

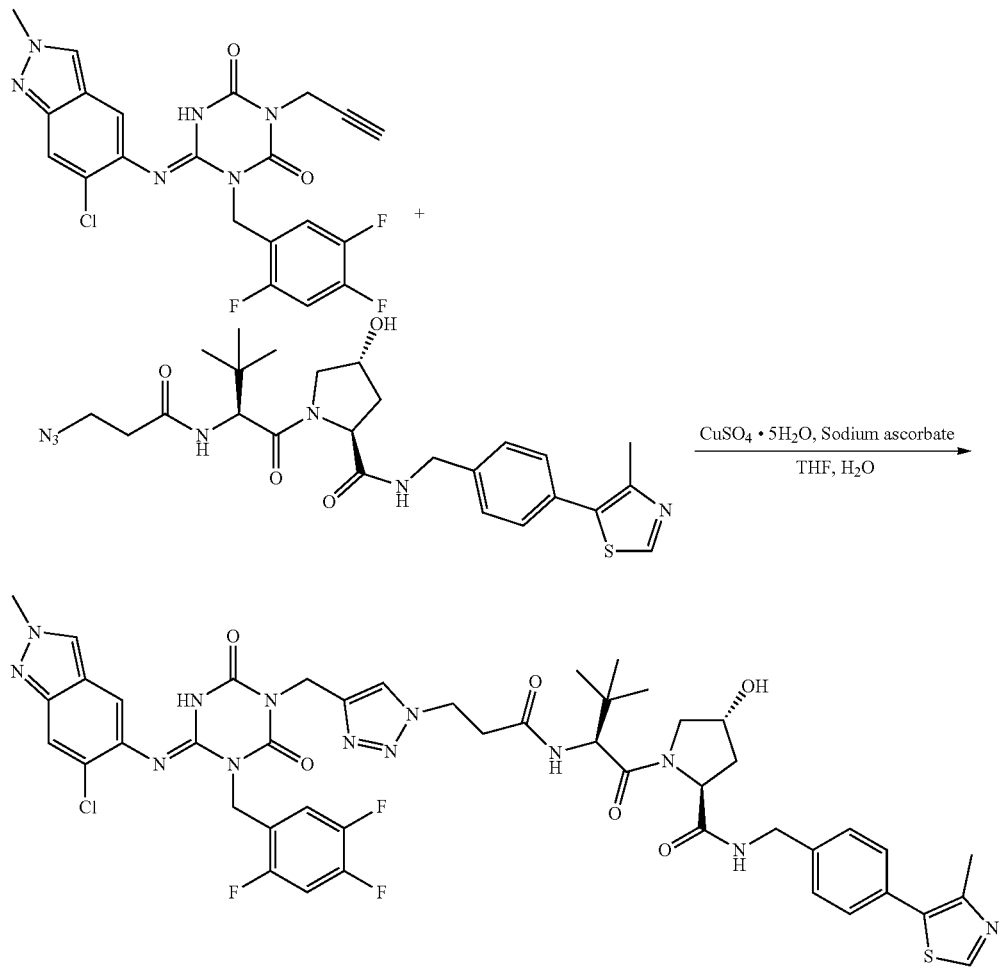

Compound a4 (142.4 mg, 0.3 mmol), compound c1 (190.0 mg, 0.36 mmol), copper sulfate pentahydrate (30.0 mg, 0.12 mmol) and sodium ascorbate (23.8 mg, 0.12 mmol) were placed in a reactor with a mixture of 10 mL tetrahydrofuran and 1 mL water. The reaction mixture was protected by argon, heated and stirred at 45° C. overnight, and monitored by TLC. After the reaction was complete, the reaction mixture was concentrated under reduced pressure to remove the solvent, separated and purified by column chromatography (dichloromethane:methanol (V:V)=15:1 as mobile phase), and dried to obtain 106.1 mg of compound 1, a yield of 35.27%.

$^1$H NMR (400 MHz, DMSO-d6) δ10.55 (s, 1H), 9.17 (s, 1H), 9.02 (s, 1H), 8.59 (t, J=8.2 Hz, 1H), 8.41 (s, 1H)), 7.89 (d, J=9.0 Hz, 1H), 7.73 (s, 1H), 7.69-7.58 (m, 2H), 7.50-7.40 (m, 4H), 7.32 (m, 1H), 5.24 (s, 2H), 5.13 (s, 2H), 5.06 (s, 1H), 4.62 (d, J=8.8 Hz, 1H), 4.54-4.43 (m, 2H), 4.36 (s, 1H), 4.23 (t, J=6.5 Hz, 2H), 4.15 (dd, J=15.6, 5.6 Hz, 1H), 4.08 (s, 3H), 3.41-3.30 (m, 2H), 2.73-2.62 (m, 2H), 2.54 (s, 3H), 1.92-1.79 (m, 2H), 0.98 (s, 9H).

$^{13}$C NMR (101 MHz, DMSO-d6) δ178.88, 175.24, 164.81, 156.92, 155.33, 153.89, 151.38, 150.91, 150.52, 149.76, 148.14, 147.87, 145.78, 144.45, 142.15, 136.67, 133.28, 129.44, 128.61, 126.99, 125.52, 122.12, 121.03, 117.89, 116.56, 116.04, 114.89, 107.54, 72.33, 66.80, 57.05, 53.78, 51.62, 49.37, 44.24, 41.87, 37.65, 34.82, 31.94, 30.93, 27.93, 16.12.

Example 2

Compound 2: Preparation of (2S,4R)-1-((S)-2-(4-(4-(((E)-4-(6-chloro-2-methyl-2H-indazol-5-yl)idene amino)-2,6-dioxy-3-(2,4,5-trifluorobenzyl)-1,3,5-triazin-1-yl)methyl)-1H-1,2,3-triazol-1-yl)butanamido)-3,3-dimethylbutyryl)-4-hydroxy-N-(4-(4-methylthiazol-5-yl)benzyl)pyrrolidine-2-carboxamide

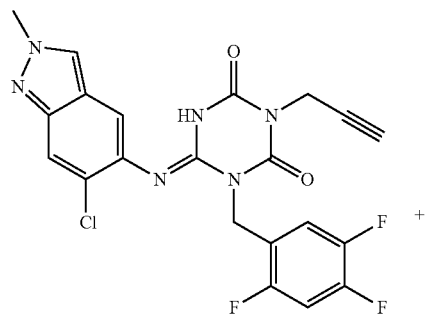

+

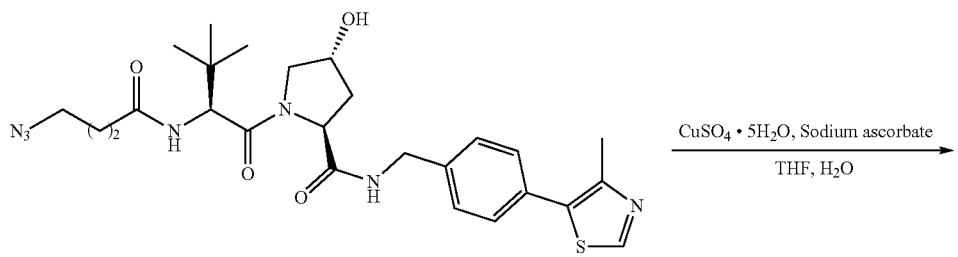

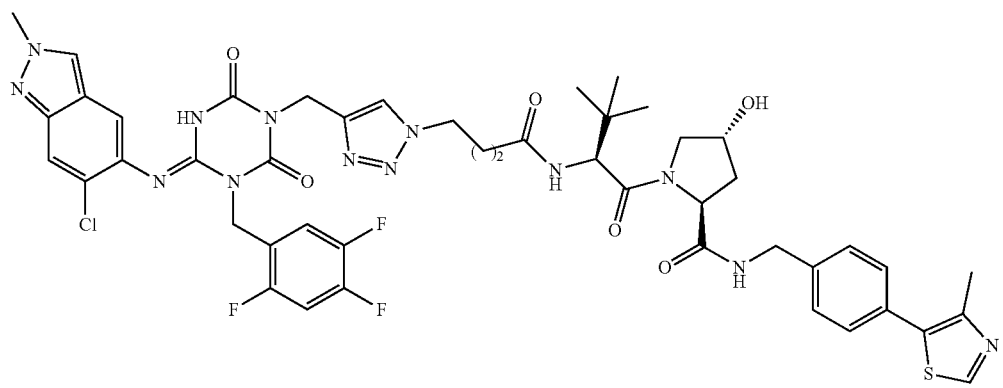

Compound 2 was prepared in the same way as Compound 1 with different starting materials, a yield of 32.62%.

$^1$H NMR (400 MHz, DMSO-d6) δ10.58 (s, 1H), 9.21 (s, 1H), 9.00 (s, 1H), 8.61 (t, J=8.4 Hz, 1H), 8.39 (s, 1H)), 7.92 (d, J=9.3 Hz, 1H), 7.75 (s, 1H), 7.71-7.60 (m, 2H), 7.52-7.40 (m, 4H), 7.35 (m, 1H), 5.28 (s, 2H), 5.17 (s, 2H), 5.08 (s, 1H), 4.58 (d, J=9.0 Hz, 1H), 4.57-4.45 (m, 2H), 4.42 (s, 1H), 4.38 (t, J=6.5 Hz, 2H), 4.26 (dd, J=15.6, 5.6 Hz, 1H), 4.20 (s, 3H), 3.42-3.30 (m, 2H), 2.58 (s, 3H), 2.34-2.23 (m, 2H), 2.10-1.99 (m, 2H), 1.89-1.77 (m, 2H), 1.01 (s, 9H).

$^{13}$C NMR (101 MHz, DMSO-d6) δ179.04, 176.32, 165.56, 156.02, 155.23, 154.33, 151.27, 150.89, 150.43, 149.46, 148.32, 147.12, 145.89, 144.62, 141.11, 136.48, 133.12, 129.24, 128.58, 126.71, 126.57, 121.34, 120.89, 117.65, 116.62, 116.21, 114.63, 106.43, 71.34, 68.69, 56.71, 54.38, 52.59, 48.34, 42.31, 40.65, 38.45, 35.78, 32.54, 31.73, 26.23, 24.22, 16.01.

Example 3

Compound 3: Preparation of (2S,4R)-1-((S)-2-(5-(4-(((E)-4-(6-chloro-2-methyl-2H-indazol-5-yl)idene amino)-2,6-dioxy-3-(2,4,5-trifluorobenzyl)-1,3,5-triazin-1-yl)methyl)-1H-1,2,3-triazol-1-yl)pentanamido)-3,3-dimethylbutyryl)-4-hydroxy-N-(4-(4-methylthiazol-5-yl)benzyl)pyrrolidine-2-carboxamide

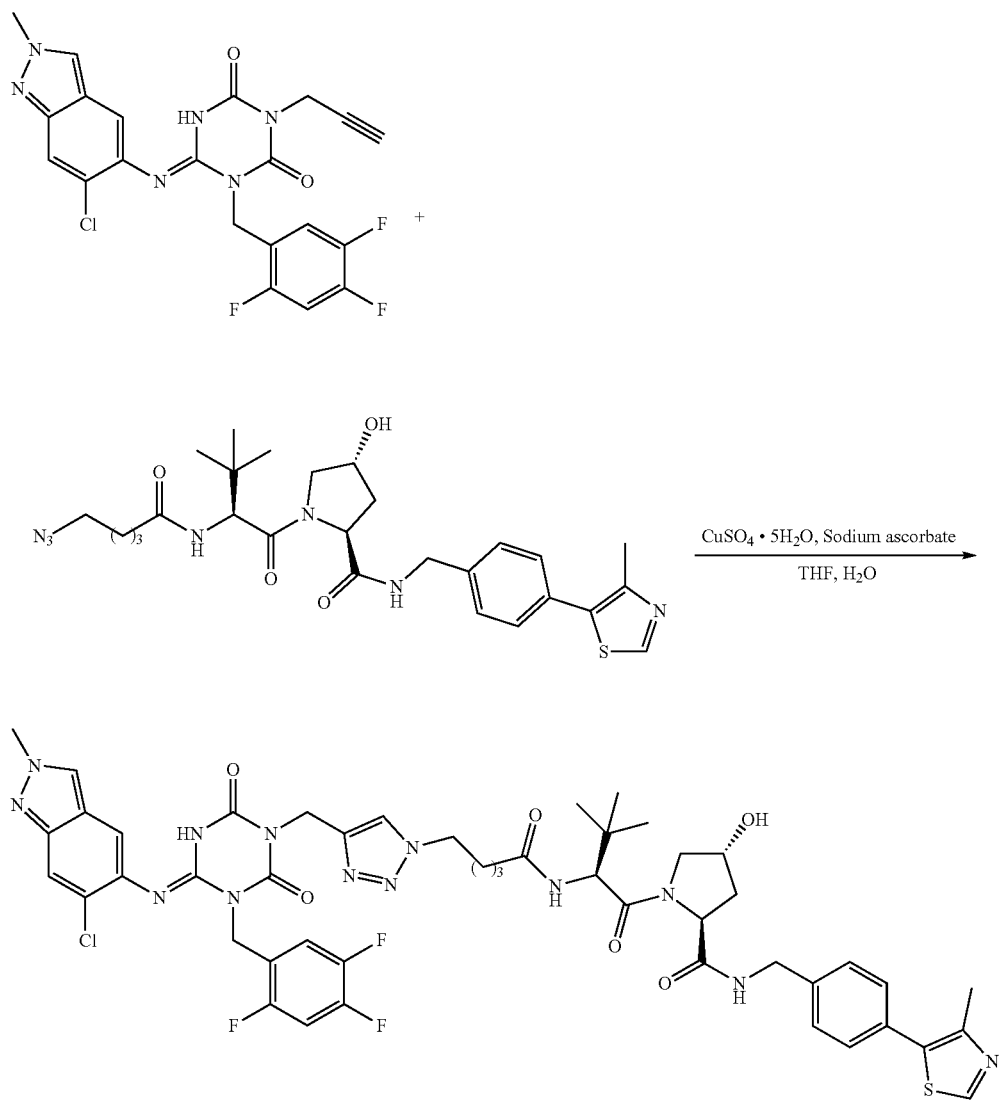

Compound 3 was prepared in the same way as Compound 1 with different starting materials, a yield of 28.28%.

$^1$H NMR (400 MHz, DMSO-d6) δ10.65 (s, 1H), 9.25 (s, 1H), 9.02 (s, 1H), 8.58 (t, J=8.5 Hz, 1H), 8.41 (s, 1H)), 7.89 (d, J=9.4 Hz, 1H), 7.72 (s, 1H), 7.69-7.58 (m, 2H), 7.50-7.39 (m, 4H), 7.33 (m, 1H), 5.32 (s, 2H), 5.19 (s, 2H), 5.12 (s, 1H), 4.62 (d, J=9.2 Hz, 1H), 4.54-4.42 (m, 2H), 4.38 (s, 1H), 4.30 (t, J=6.8 Hz, 2H), 4.24 (dd, J=15.8, 6.0 Hz, 1H), 4.12 (s, 3H), 3.38-3.27 (m, 2H), 2.65 (s, 3H), 2.48-2.38 (m, 2H), 2.06-1.94 (m, 2H), 1.90-1.79 (m, 2H), 1.71-1.60 (m, 2H), 1.02 (s, 9H).

$^{13}$C NMR (101 MHz, DMSO-d6) δ178.89, 175.17, 164.45, 155.92, 156.23, 154.23, 151.12, 150.62, 150.37, 149.83, 148.12, 146.85, 145.91, 144.64, 141.06, 136.45, 133.02, 129.14, 128.55, 126.68, 126.45, 121.24, 120.71, 117.45, 116.74, 116.31, 114.58, 106.23, 72.27, 69.35, 57.76, 55.57, 51.73, 45.52, 41.45, 40.38, 39.02, 36.45, 34.74, 29.23, 27.21, 25.89, 23.72, 15.44.

Example 4

Compound 4: Preparation of pyrrolidine-2-carboxamide of (2S,4R)-1-((S)-2-(6-(4-(((E)-4-(6-chloro-2-methyl-2H-indazol-5-yl)idene amino)-2,6-dioxy-3-(2,4,5-trifluorobenzyl)-1,3,5-triazin-1-yl)methyl)-1H-1,2,3-Triazol-1-yl)hexamido)-3,3-dimethylbutyryl)-4-hydroxy-N-(4-(4-methylthiazol-5-yl)benzyl)pyrrolidine-2-carboxamide

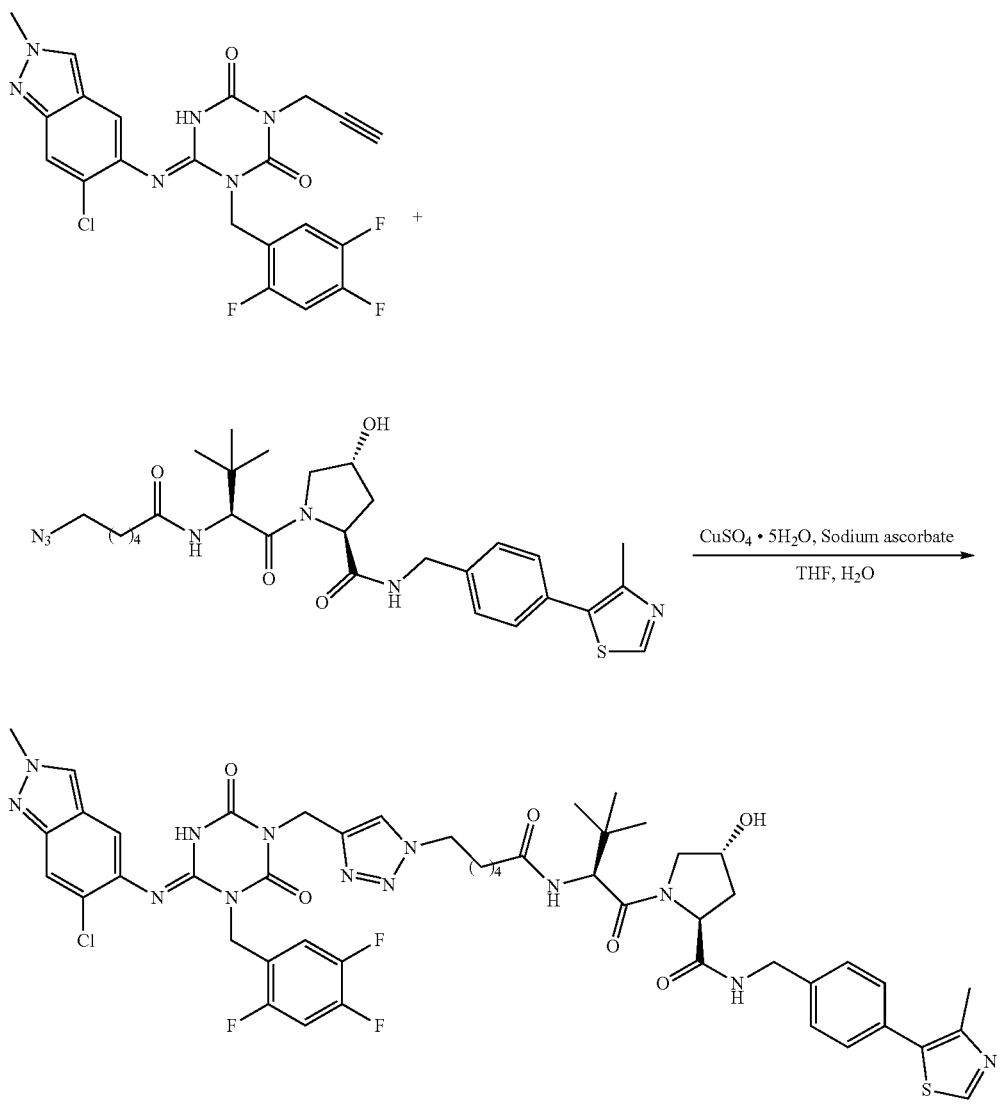

Compound 4 was prepared in the same way as Compound 1 with different starting materials, a yield of 24.29%.

$^1$H NMR (400 MHz, DMSO-d6) δ10.51 (s, 1H), 9.19 (s, 1H), 9.03 (s, 1H), 8.60 (t, J=8.6 Hz, 1H), 8.39 (s, 1H)), 7.91 (d, J=9.8 Hz, 1H), 7.76 (s, 1H), 7.71-7.60 (m, 2H), 7.52-7.41 (m, 4H), 7.37 (m, 1H), 5.29 (s, 2H), 5.15 (s, 2H), 5.13 (s, 1H), 4.62 (d, J=9.4 Hz, 1H), 4.58-4.46 (m, 2H), 4.42 (s, 1H), 4.34 (t, J=7.2 Hz, 2H), 4.28 (dd, J=16.0, 6.1 Hz, 1H), 4.16 (s, 3H), 3.42-3.30 (m, 2H), 2.67 (s, 3H), 2.52-2.38 (m, 2H), 1.98-1.87 (m, 2H), 1.85-1.71 (m, 4H), 1.54-1.42 (m, 2H), 0.96 (s, 9H).

$^{13}$C NMR (101 MHz, DMSO-d6) δ179.23, 175.22, 164.33, 155.90, 156.12, 154.12, 150.98, 150.54, 150.48, 149.78, 148.04, 146.76, 145.89, 144.56, 141.12, 136.27, 132.89, 128.97, 128.45, 126.62, 126.37, 121.13, 120.68, 117.34, 116.67, 116.24, 114.45, 106.31, 72.18, 68.45, 58.36, 57.27, 53.83, 44.36, 40.71, 40.44, 38.29, 36.19, 35.64, 28.91, 28.18, 27.62, 26.25, 23.42, 16.38.

Example 5

Compound 5: Preparation of (2S,4R)-1-((S)-2-(7-(4-(((E)-4-(6-chloro-2-methyl-2H-indazol-5-yl)idene amino)-2,6-dioxy-3-(2,4,5-trifluorobenzyl)-1,3,5-triazin-1-yl)methyl)-1H-1,2,3-Triazol-1-yl)heptamido)-3,3-dimethylbutyryl)-4-hydroxy-N-(4-(4-methylthiazol-5-yl)benzyl)pyrrolidine-2-carboxamide

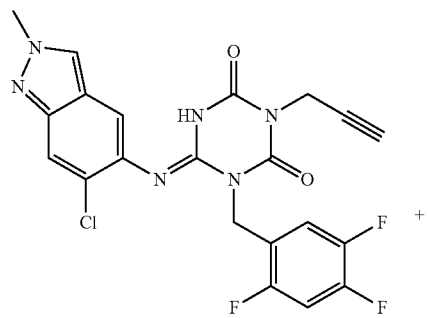

+

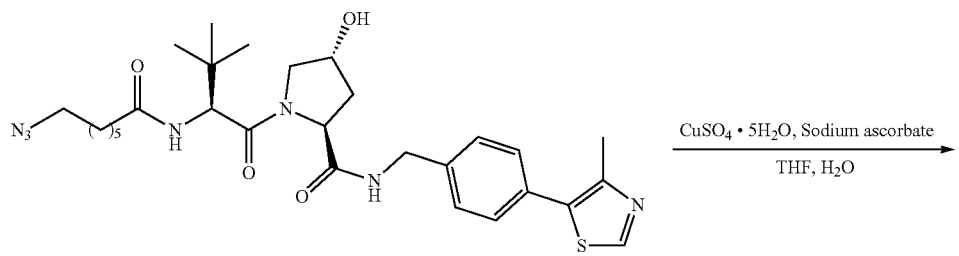

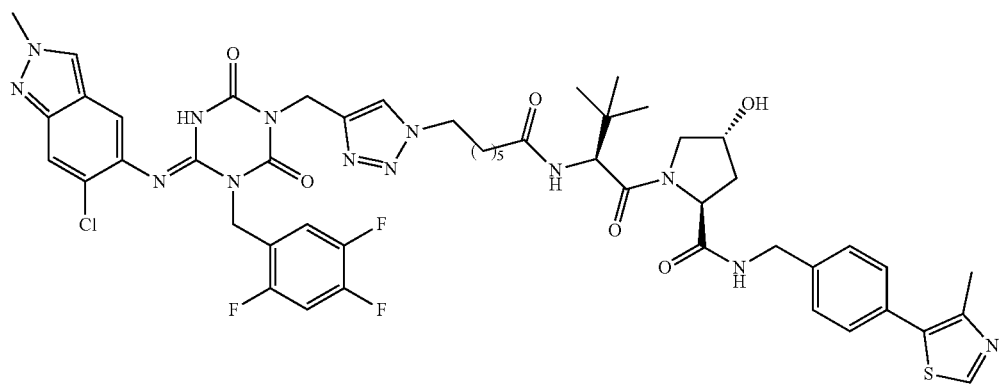

Compound 5 was prepared in the same way as Compound 1 with different starting materials, a yield of 20.97%.

$^1$H NMR (400 MHz, DMSO-d6) δ10.58 (s, 1H), 9.27 (s, 1H), 9.00 (s, 1H), 8.58 (t, J=8.3 Hz, 1H), 8.39 (s, 1H)), 7.92 (d, J=9.4 Hz, 1H), 7.76 (s, 1H), 7.65-7.53 (m, 2H), 7.50-7.39 (m, 4H), 7.35 (m, 1H), 5.29 (s, 2H), 5.12 (s, 2H), 5.11 (s, 1H), 4.62 (d, J=10.2 Hz, 1H), 4.51-4.40 (m, 2H), 4.37 (s, 1H), 4.34 (t, J=6.6 Hz, 2H), 4.22 (dd, J=16.0, 5.8 Hz, 1H), 4.09 (s, 3H), 3.27-3.15 (m, 2H), 2.52 (s, 3H), 2.44-2.32 (m, 2H), 1.93-1.81 (m, 2H), 1.78-1.66 (m, 4H), 1.44 (s, 4H), 0.98 (s, 9H).

$^{13}$C NMR (101 MHz, DMSO-d6) δ177.92, 173.64, 164.12, 155.94, 155.82, 153.43, 151.29, 150.71, 150.78, 148.90, 148.11, 146.78, 146.25, 144.43, 141.21, 136.27, 132.76, 129.34, 128.46, 126.62, 126.38, 121.44, 120.98, 117.27, 117.08, 116.63, 114.34, 106.42, 72.26, 68.56, 58.21, 57.36, 52.83, 44.42, 40.71, 40.34, 38.28, 36.19, 35.72, 33.26, 28.93, 28.17, 27.63, 26.12, 25.13, 16.32.

Example 6

Compound 6: Preparation of (2S,4R)-1-((S)-2-(8-(4-(((E)-4-(6-chloro-2-methyl-2H-indazol-5-yl)idene amino)-2,6-dioxy-3-(2,4,5-trifluorobenzyl)-1,3,5-triazin-1-yl)methyl)-1H-1,2,3-Triazol-1-yl)octamido)-3,3-dimethylbutyryl)-4-hydroxy-N-(4-(4-methylthiazol-5-yl)benzyl)pyrrolidine-2-carboxamide

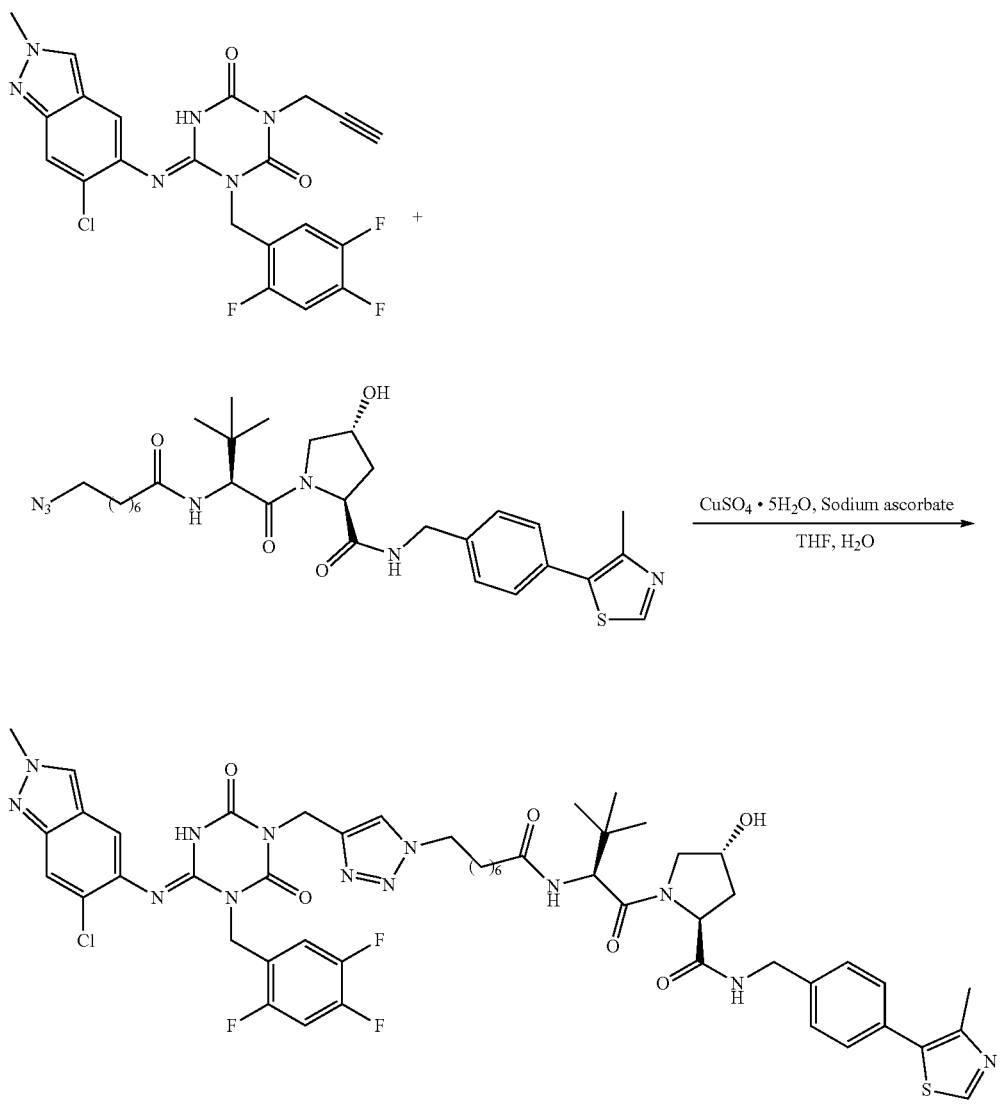

Compound 6 was prepared in the same way as Compound 1 with different starting materials, a yield of 17.83%.

$^1$H NMR (400 MHz, DMSO-d6) δ10.54 (s, 1H), 9.22 (s, 1H), 9.00 (s, 1H), 8.54 (t, J=8.2 Hz, 1H), 8.41 (s, 1H)), 7.87 (d, J=9.5 Hz, 1H), 7.74 (s, 1H), 7.67-7.54 (m, 2H), 7.48-7.38 (m, 4H), 7.33 (m, 1H), 5.31 (s, 2H), 5.14 (s, 2H), 5.10 (s, 1H), 4.57 (d, J=9.5 Hz, 1H), 4.53-4.41 (m, 2H), 4.39 (s, 1H), 4.30 (t, J=6.7 Hz, 2H), 4.25 (dd, J=15.9, 5.6 Hz, 1H), 4.12 (s, 3H), 3.23-3.11 (m, 2H), 2.47 (s, 3H), 2.32-2.21 (m, 2H), 1.89-1.75 (m, 2H), 1.72-1.57 (m, 4H), 1.36 (s, 6H), 0.97 (s, 9H).

$^{13}$C NMR (101 MHz, DMSO-d6) δ178.21, 173.24, 165.35, 156.20, 155.78, 153.42, 151.27, 150.67, 150.53, 149.13, 147.68, 146.42, 146.03, 144.23, 140.81, 136.27, 132.56, 129.28, 128.44, 126.58, 126.37, 120.98, 120.70, 117.22, 116.89, 116.49, 114.21, 106.21, 72.19, 68.45, 58.36, 57.25, 52.48, 44.33, 40.67, 40.20, 38.14, 36.13, 35.68, 34.91, 33.28, 28.92, 28.14, 27.66, 25.90, 24.91, 15.48.

Example 7

Compound 7: Preparation of (2S,4R)-1-((S)-2-(2-(2-(4-(((E)-4-((6-chloro-2-methyl-2H-indazole-5-yl)imino)-2,6-dioxy-3-(2,4,5-trifluorobenzyl)-1,3,5-triazin-1-yl)methyl)-1H-1,2,3-Triazol-1-yl)ethoxy)acetamido)-3,3-dimethylbutyryl)-4-hydroxy-N-(4-(4-methylthiazol-5-yl))benzyl)pyrrolidine-2-carboxamide (1) Preparation of Compound a4

The preparation method was the same as in Example 1.

(2) Preparation of Compound d1

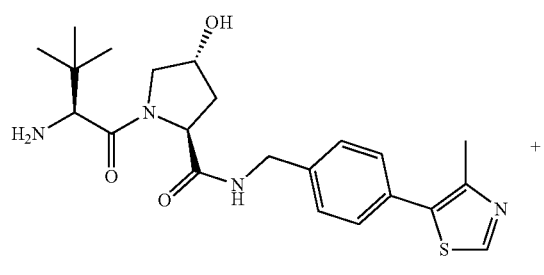

+

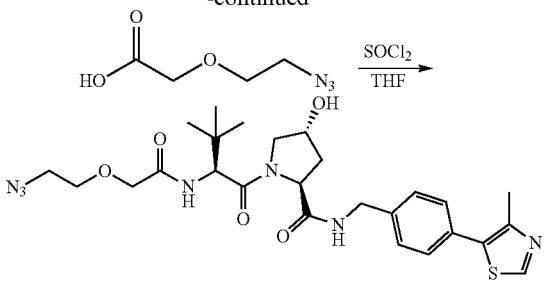

2-(2-Azidoethoxy)acetic acid (290.2 mg, 2 mmol) was dissolved in 5 mL of thionyl chloride, and heated under reflux for 2 hours. After the reaction was complete, the reaction mixture was concentrated under reduced pressure to remove the solvent, and then added (S, R, S)-AHPC (1 mmol, 430.6 mg) and 10 mL of tetrahydrofuran as a solvent. The reaction mixture was heated under reflux for 5 hours and monitored by TLC. After the reaction was completed, the reaction mixture was cooled to room temperature, added 2 mL of methanol, and stirred for 1 hour. The solvent was removed by concentration under reduced pressure, and 407.0 mg of compound d1 was obtained by column chromatography (eluent: dichloromethane:methanol (V:V)=10:1), a yield of 72.98%.

(3) Preparation of compound 7

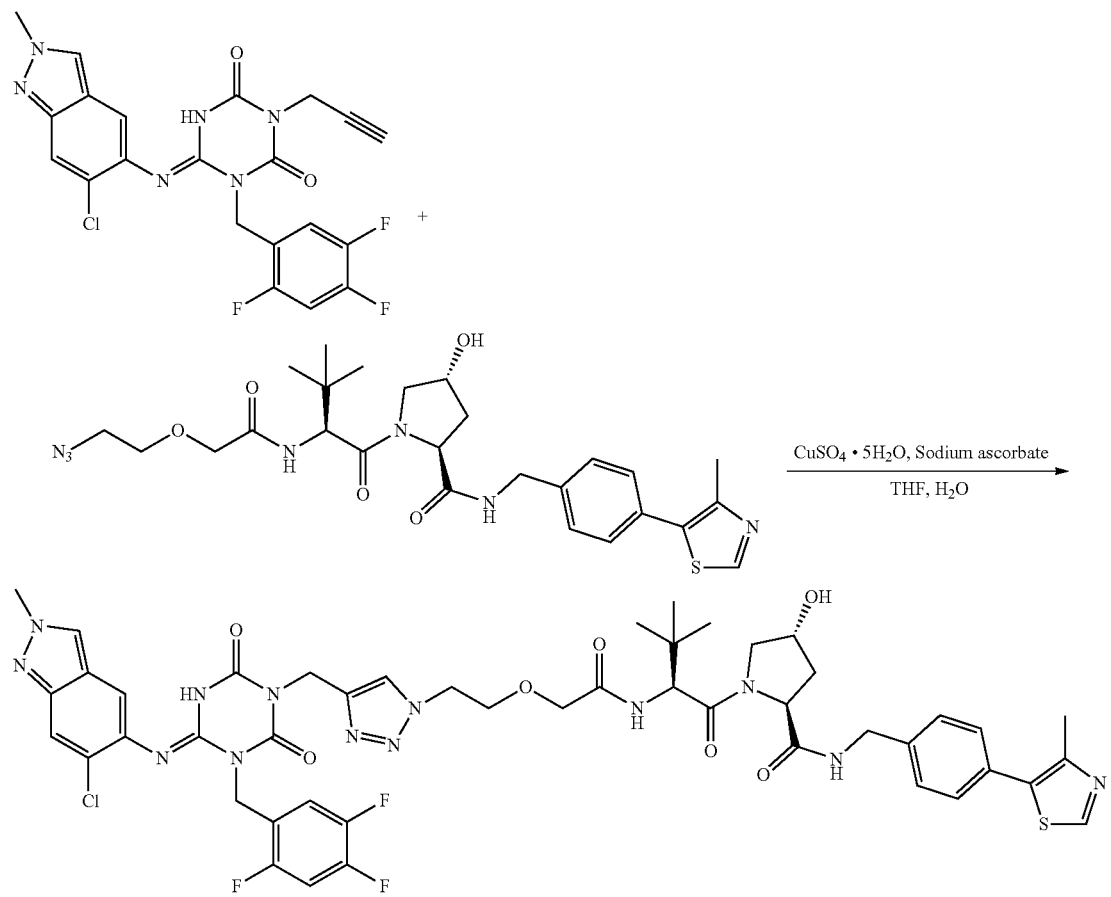

Compound a4 (142.4 mg, 0.3 mmol), compound d1 (200.7 mg, 0.36 mmol), copper sulfate pentahydrate (30.0 mg, 0.12 mmol) and sodium ascorbate (23.8 mg, 0.12 mmol) were placed in a reactor with a mixture of 10 mL tetrahydrofuran and 1 mL water. The reaction mixture was protected by argon, heated and stirred at 45° C. overnight, and monitored by TLC. After the reaction was completed, the reaction mixture was concentrated under reduced pressure to remove the solvent, separated and purified by column chromatography (dichloromethane:methanol (V:V)=20:1 as mobile phase), and dried to obtain 82.5 mg of compound 7, a yield of 26.63%.

$^1$H NMR (400 MHz, DMSO-d6) δ10.44 (s, 1H), 9.15 (s, 1H), 8.92 (s, 1H), 8.51 (t, J=8.0 Hz, 1H), 8.28 (s, 1H)), 7.87 (d, J=9.2 Hz, 1H), 7.71 (s, 1H), 7.65-7.54 (m, 2H), 7.48-7.38 (m, 4H), 7.29 (m, 1H), 5.17 (s, 2H), 5.13 (s, 2H), 5.05 (s, 1H), 4.62 (d, J=9.0 Hz, 1H), 4.54-4.43 (m, 2H), 4.38 (s, 1H), 4.30 (t, J=6.6 Hz, 2H), 4.24 (dd, J=15.6, 5.6 Hz, 1H), 4.16 (s, 3H), 4.02-3.89 (m, 2H), 3.58 (s, 2H), 3.38-3.26 (m, 2H), 2.61 (s, 3H), 1.94-1.83 (m, 2H), 0.95 (s, 9H).

$^{13}$C NMR (101 MHz, DMSO-d6) δ178.99, 175.44, 164.23, 156.18, 155.55, 154.23, 151.17, 150.78, 150.22, 149.58, 148.67, 147.55, 145.78, 144.34, 142.33, 135.52, 132.14, 129.58, 128.76, 126.90, 125.67, 122.12, 121.15, 117.45, 116.56, 116.33, 114.56, 108.58, 72.41, 71.12, 69.16, 67.32, 57.51, 55.42, 52.59, 47.24, 44.61, 42.47, 39.48, 36.12, 32.84, 27.45, 16.23.

Example 8

Compound 8: Preparation of (2S,4R)-1-((S)-2-(2-(2-(2-(4-(((E)-4-((6-chloro-2-methyl-2H-indazole)-5-yl)imino)-2,6-dioxy-3-(2,4,5-trifluorobenzyl)-1,3,5-triazin-1-yl)methyl)-1H-1,2,3-Triazol-1-yl)ethoxy)ethoxy)acetamido)-3,3-dimethylbutyryl)-4-hydroxy-N-(4-(4-Methylthiazol-5-yl)benzyl)pyrrolidine-2-carboxamide

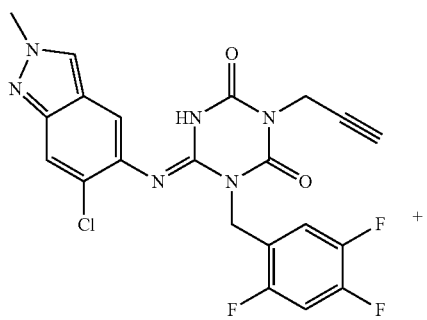

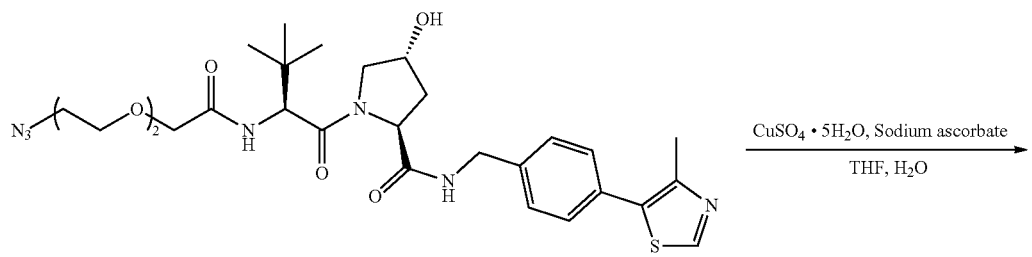

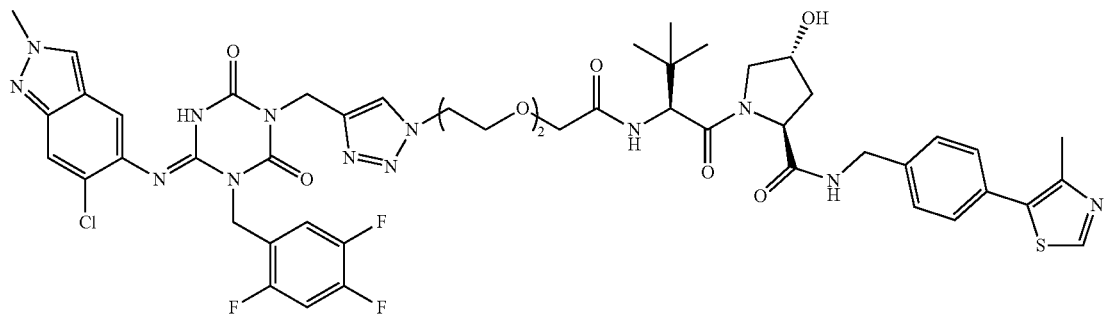

Compound 8 was prepared in the same way as compound 7 with different starting materials, a yield of 21.89%.

$^1$H NMR (400 MHz, DMSO-d6) δ10.52 (s, 1H), 9.18 (s, 1H), 8.95 (s, 1H), 8.50 (t, J=8.2 Hz, 1H), 8.32 (s, 1H)), 7.91 (d, J=9.2 Hz, 1H), 7.73 (s, 1H), 7.66-7.56 (m, 2H), 7.52-7.40 (m, 4H), 7.31 (m, 1H), 5.21 (s, 2H), 5.10 (s, 2H), 5.03 (s, 1H), 4.58 (d, J=9.2 Hz, 1H), 4.50-4.41 (m, 2H), 4.34 (s, 1H), 4.28 (t, J=6.6 Hz, 2H), 4.22 (dd, J=15.8, 5.6 Hz, 1H), 4.17 (s, 3H), 4.09-3.98 (m, 2H), 3.63 (s, 2H), 3.45 (s, 4H), 3.36-3.24 (m, 2H), 2.59 (s, 3H), 1.97-1.87 (m, 2H), 0.98 (s, 9H).

$^{13}$C NMR (101 MHz, DMSO-d6) δ179.07, 175.78, 166.45, 156.56, 155.24, 154.76, 152.27, 151.16, 150.78, 149.35, 148.76, 147.63, 146.32, 144.46, 142.89, 136.91, 131.36, 129.07, 127.86, 126.53, 125.72, 122.45, 121.63, 117.83, 116.95, 116.35, 114.67, 109.45, 73.78, 71.48, 70.23, 68.71, 68.32, 66.62, 58.31, 55.34, 51.60, 48.64, 45.33, 43.28, 39.79, 36.55, 33.21, 27.28, 15.90.

Example 9

Compound 9: Preparation of (2S,4R)-1-((S)-2-(tert-butyl)-14-(4-(((E)-4-((6-chloro-2-methyl-2H-indazole-5-yl)imino)-2,6-dioxy-3-(2,4,5-trifluorobenzyl)-1,3,5-triazin-1-yl)methyl)-1H-1,2,3-Triazol-1-yl)-4-oxo-6,9,12-triazole-3-azatetradecyl)-4-hydroxy-N-(4-(4-Methylthiazol-5-yl)benzyl)pyrrolidine-2-carboxamide Compound 9 was prepared in the same way as compound 7 with different starting materials, a yield of 17.42%.

$^1$H NMR (400 MHz, DMSO-d6) δ10.56 (s, 1H), 9.22 (s, 1H), 9.01 (s, 1H), 8.56 (t, J=8.4 Hz, 1H), 8.36 (s, 1H)), 7.89 (d, J=9.0 Hz, 1H), 7.72 (s, 1H), 7.64-7.54 (m, 2H), 7.48-7.36 (m, 4H), 7.28 (m, 1H), 5.28 (s, 2H), 5.15 (s, 2H), 5.09 (s, 1H), 4.62 (d, J=9.4 Hz, 1H), 4.52-4.40 (m, 2H), 4.32 (s, 1H), 4.26 (t, J=6.5 Hz, 2H), 4.20 (dd, J=16.0, 6.2 Hz, 1H), 4.14 (s, 3H), 4.06-3.95 (m, 2H), 3.67 (s, 2H), 3.52 (s, 8H), 3.38-3.30 (m, 2H), 2.62 (s, 3H), 1.94-1.83 (m, 2H), 0.96 (s, 9H)

$^{13}$C NMR (101 MHz, DMSO-D6) δ 178.77, 176.23, 167.41, 156.78, 155.45, 153.03, 152.36, 151.90, 149.83, 147.45, 145.42, 138.26, 138.26, 138.26, 138.26, 138.26, 138.26, 138.26, 138.26, 138.26, 138.26, 138.26, 138.26, 138.26, 138.26, 138.26, 138.26, 138.26, 138.26, 138.26, 138. 32.81, 26.88, 15.78.

2. Bioactivity Assay (1) 3CL$^{pro}$ Inhibitory Activity Test

The inhibitory activity of the compounds against SARS-CoV-2 3CL$^{pro}$ was determined using fluorescence resonance energy transfer.

10 μL of the compound solutions prepared at different concentrations (final concentrations of 1000, 500, 250, 125, 62.5, 31.25, 15.63, 7.81, 3.90, 1.95 nM, in DMSO) and 40 μL of SARS-CoV-2 3CL$^{pro}$ (Shanghai Biyuntian Biotechnology Co., Ltd., final concentration: 0.5 μM, diluted with

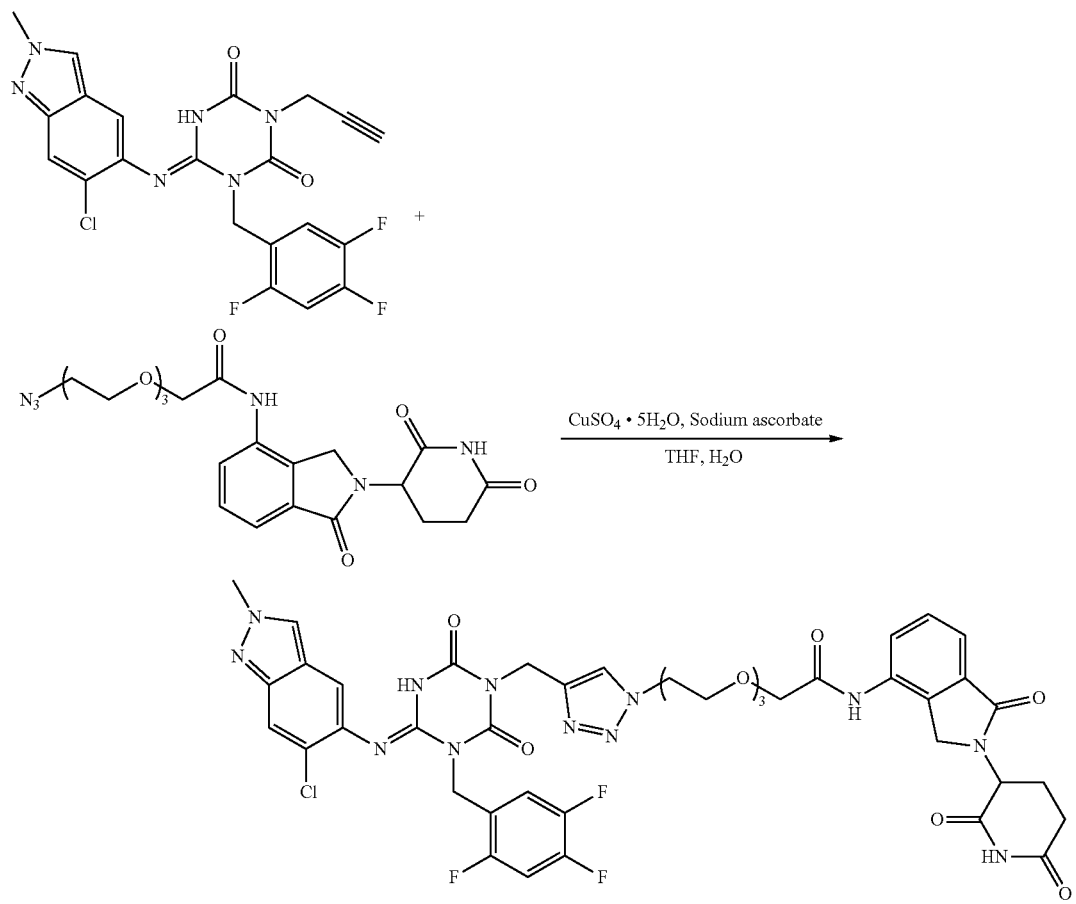

Tris-HCl buffer (20 mM Tris-HCl, 100 mM NaCl, 1 mM EDTA, pH 7.4)) were mixed, added to a black 96-well plate, incubate at 37° C. for 10 min. A reaction was initiated by adding 50 μL of the fluorescent substrate Dabcyl-KT-SAVLQSGFRKME-Edans (Shanghai Biyuntian Biotechnology Co., Ltd., the final concentration: 20 μM), incubated for 10 min, and measured by a multifunctional microplate reader (Thermo Fisher Scientific Co., Ltd., Varioskan Flash) for fluorescence detection, the excitation wavelength: 340 nm, the emission wavelength: 490 nm. The fluorescence value was recorded to calculate the inhibition percentage of the sample. DMSO without compound was used as the enzyme activity control, and the Tris-HCl buffer without SARS-CoV-2 3CL$^{pro}$ was used as the blank control, and the treatment methods were the same. The IC$_{50}$ values of the samples (compounds 1-9) were calculated by nonlinear regression analysis using GraphPad Prism software.

Inhibition Rate (%)=(RFU$_{enzyme\ activity\ control}$−RFU$_{sample}$)/(RFU$_{enzyme\ activity\ control}$−RFU$_{blank\ control}$)×100%

The experimental results are shown in Table 1 (in Table 1, the column of IC$_{50}$, A: IC50<100 nM, B: IC$_{50}$=100-1000 nM), the example compounds all have inhibitory activity against 3CL$^{pro}$, among which compounds 4, 5, 6, 8, and 9 have strong inhibitory effects on 3CL$^{pro}$, with IC$_{50}$ values below 100 nM.

(2) Determination of 3CL$^{pro}$ Degradation Activity by Western Blot

HEK293E cells in logarithmic growth phase (the Cell Bank of the Chinese Academy of Sciences) were seeded in a 6-well plate at a density of 6.0×105 cells/well, and incubated in a 37° C. incubator with 5% CO2 for 8-24 h. When the density reached 70% confluence, the plate was replaced with 2 mL of pre-warmed serum-free medium (Shanghai Opmax Biotechnology Co., Ltd.). The SARS-CoV-2 3CL$^{pro}$ expression plasmid (2 μg/well, prepared in 1×HBS, Beijing Yiqiao Shenzhou Technology Co., Ltd.) was transfected with 10 μM PEI (polyethyleneimine, Shanghai McLean Biochemical Technology Co., Ltd.) at a mass-to-volume ratio of 3:4. The PEI-plasmid mixture was added dropwise to the above serum-free medium, gently shaken mixed, and incubated in a 37° C. incubator containing 5% CO$_2$ for 10 h. The medium containing transfection reagent was removed and medium containing gradient concentrations of the samples to be tested (final sample concentrations of 1000, 500, 250, 125, 62.5, 31.25, 15.63, 7.81, 3.90, 1.95 nM) was added. After culturing at 37° C. and 5% CO$_2$ for 24 h, the supernatant was discarded, the cells were collected, and RIPA cell lysis buffer (Shanghai McLean Biochemical Technology Co., Ltd.) was added to lyse the cells on ice for 30 min, and the expression of 3CL$^{pro}$ was detected by Western Blot. Image J analyzed the relative expression of 3CL$^{pro}$ and calculated the protein degradation rate. The medium without the sample to be tested was used as the control group, and the rest of the treatment methods were the same. The protein degradation activity (DC$_{50}$) of the samples was calculated by nonlinear regression analysis using GraphPad Prism software.

Degradation rate (%)=(3CL$^{pro}$ relative expression$_{control\ group}$−3CL$^{pro}$ relative$_{sample\ group}$)/3CL$^{pro}$ relative$_{control\ group}$×100%

The experimental results are shown in Table 1 (in Table 1, DC$_{50}$ is in the column, A: DC$_{50}$<100 nM, B: DC$_{50}$=100-1000 nM), the example compounds all have degrading activity on 3CLpro, among which compounds 5, 6, and 8 had stronger degradation activities against 3CL$^{pro}$, and the DC$_{50}$ values were all below 100 nM.

TABLE 1

Inhibitory activity and degradation activity of compounds 1-9 on 3CL$^{pro}$

| Compound Nos. | IC$_{50}$ (nM) | DC$_{50}$ (nM) |
| --- | --- | --- |
| 1 | B | B |
| 2 | B | B |
| 3 | B | B |
| 4 | A | B |
| 5 | A | A |
| 6 | A | A |
| 7 | B | B |
| 8 | A | A |
| 9 | A | B |

The data in Table 1 shows that compounds 1-9 have different degrees of inhibition and degradation of 3CL$^{pro}$. The IC$_{50}$ and DC$_{50}$ values of compounds 5, 6, and 8 against 3CL$^{pro}$ are all less than 100 nM. It also shows that the compounds of the present invention have both inhibitory activity and good degradation activity on 3CL$^{pro}$, and can be developed and studied as anti-coronavirus candidate drugs.

The above content is only to illustrate the technical idea of the present invention, and cannot limit the protection scope of the present invention. Any modification made on the basis of the technical solution proposed in accordance with the technical idea of the present invention falls within the scope of the claims of the present invention.

The invention claimed is:

1. A compound of formula I or formula II, a pharmaceutically acceptable salt, a diastereomer, or a tautomer thereof:

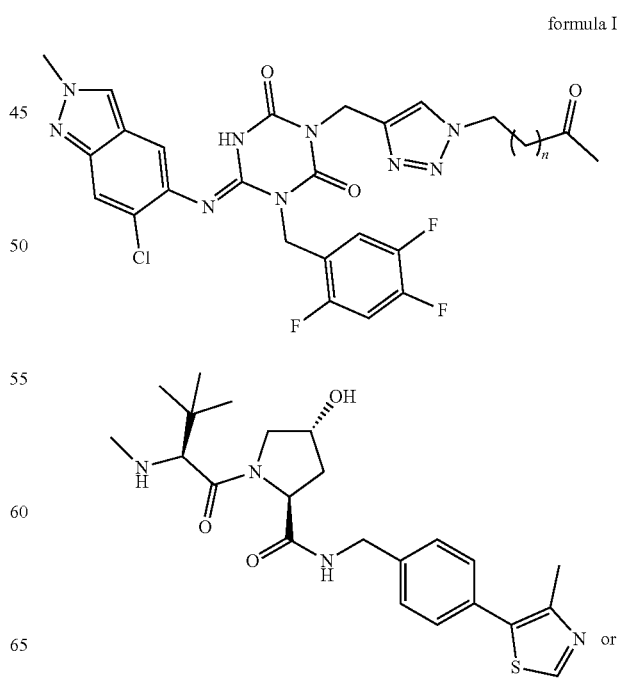

formula I or

-continued
formula II
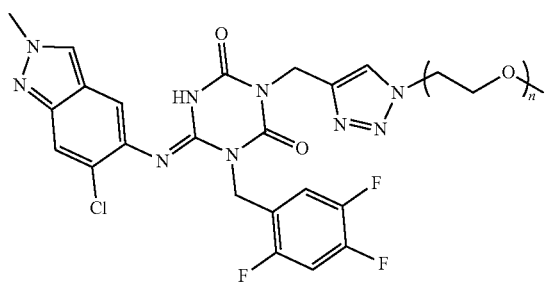
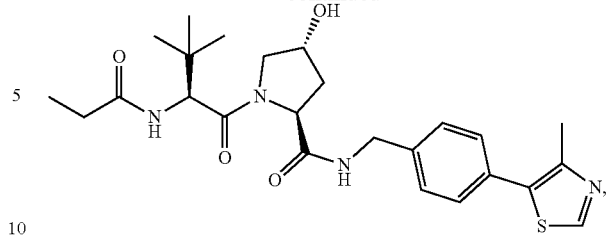
wherein, n is 1-6.
2. The compound of claim 1, wherein the compound is selected from the group consisting of:
1
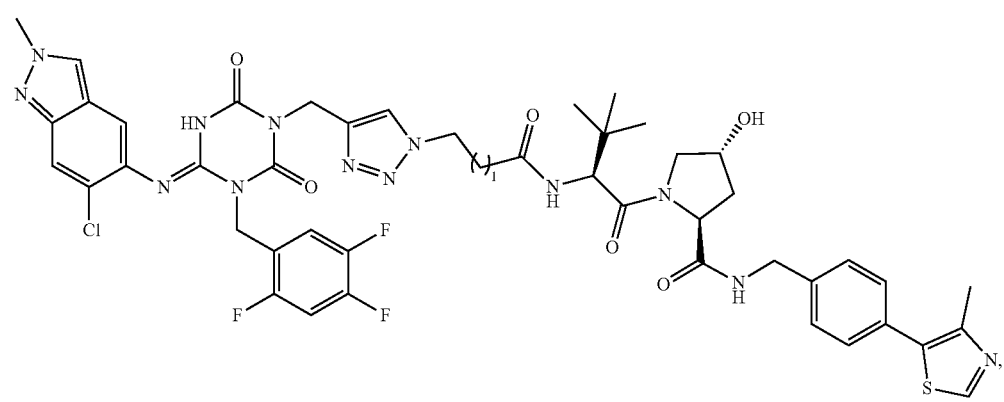
2
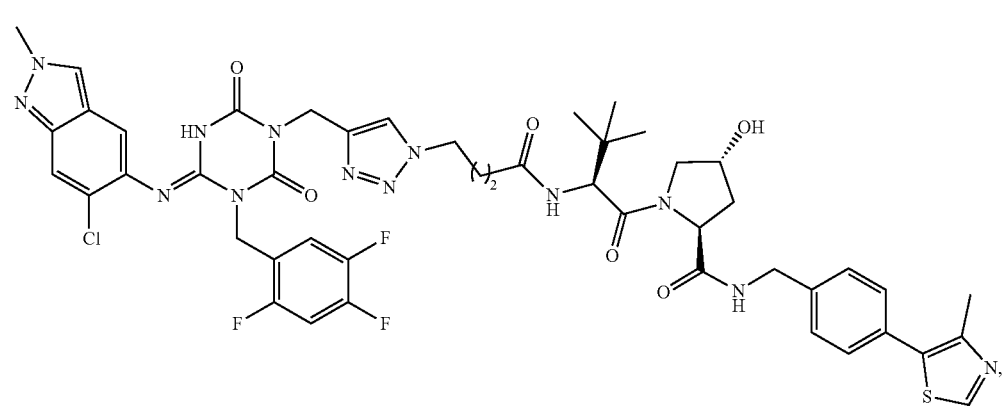
3
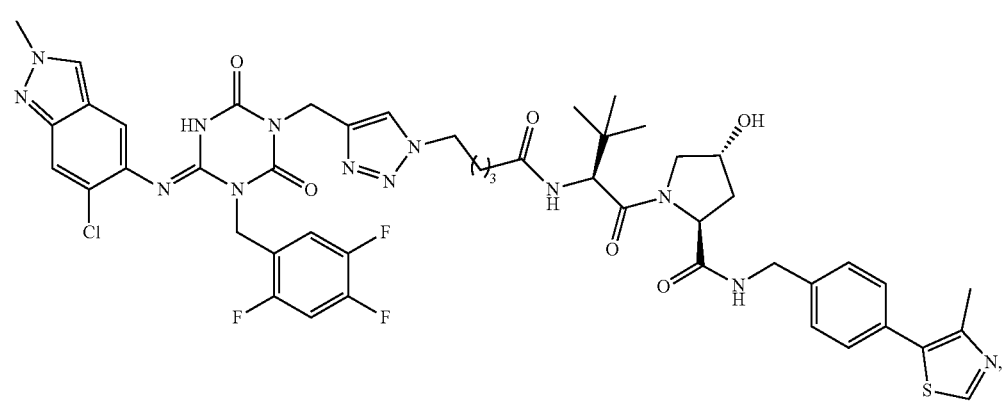

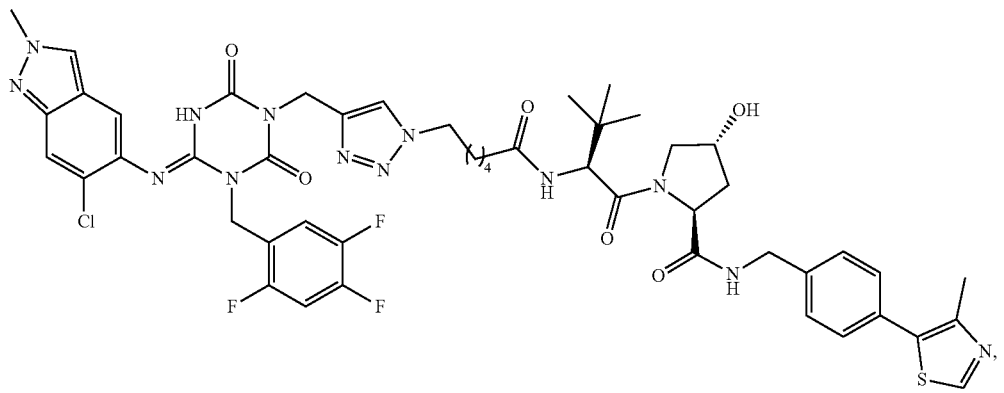
4
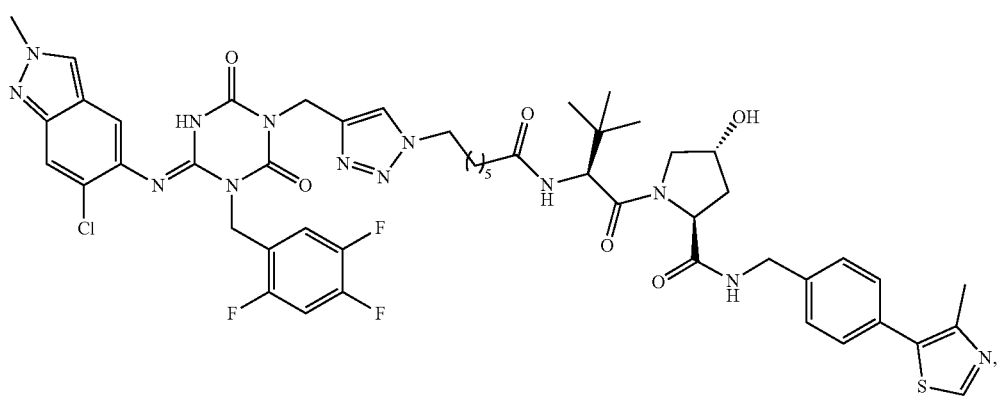
5
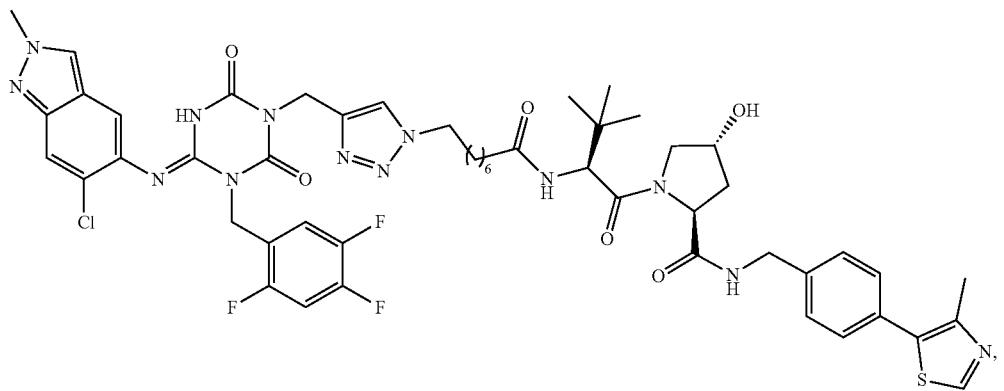
6
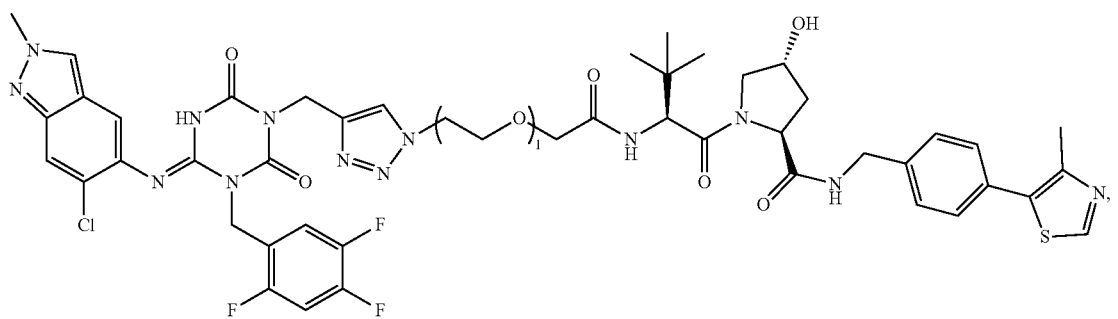
7

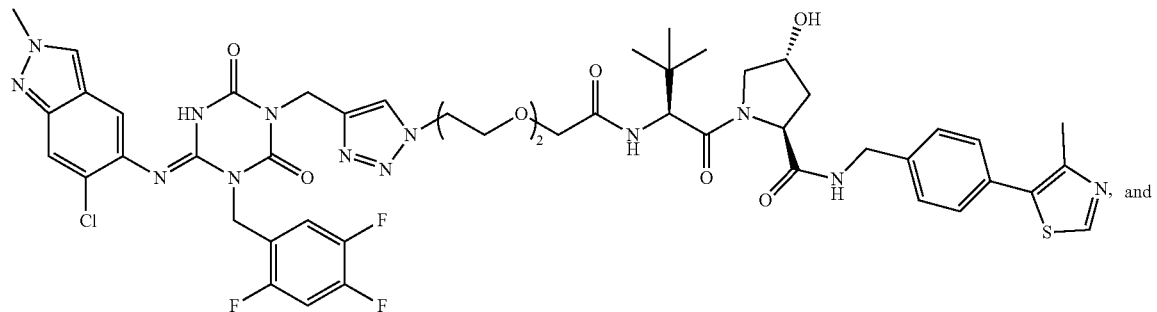

8

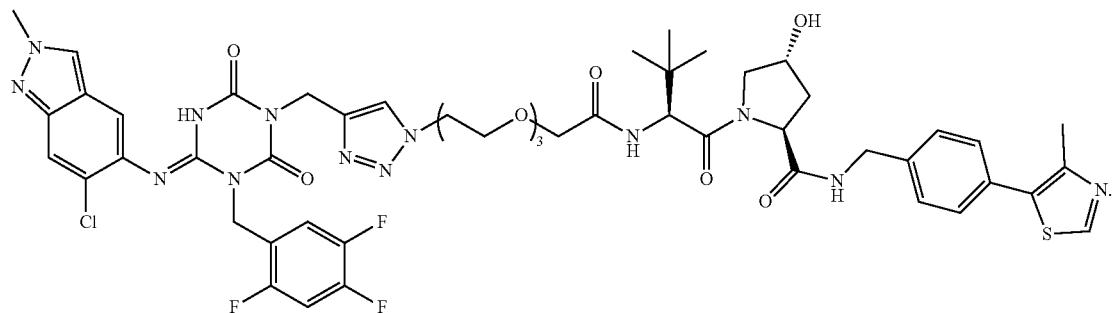

9

3. The compound of claim 1, wherein the pharmaceutically acceptable salt comprises one selected from the group consisting of hydrochloric acid, hydrobromic acid, sulfuric acid, nitric acid, phosphoric acid, acetic acid, fumaric acid, maleic acid, oxalic acid, malonic acid, succinic acid, citric acid, malic acid, methanesulfonic acid, ethanesulfonic acid, benzenesulfonic acid, toluenesulfonic acid, glutamic acid, and aspartic acid.

4. An anti-coronavirus pharmaceutical composition comprising the compound of claim 1 and a pharmaceutically acceptable carrier.

* * * * *